US011331376B2

(12) United States Patent
Yang et al.

(10) Patent No.: US 11,331,376 B2
(45) Date of Patent: May 17, 2022

(54) ORAL ADMINISTRATION OF UNSTABLE OR POORLY-ABSORBED DRUGS

(71) Applicant: InnoPharmax, Inc., Taipei (TW)

(72) Inventors: Yu-Tsai Yang, Hualien (TW);
Jong-Jing Wang, New Taipei (TW);
Pei-Jing Hsu, Meishan Township (TW);
Li-Chien Chang, Taipei (TW);
Wei-Hua Hao, Taipei (TW);
Chang-Shan Hsu, Taipei (TW)

(73) Assignee: INNOPHARMAX, INC., Taipei (TW)

( * ) Notice: Subject to any disclaimer, the term of this patent is extended or adjusted under 35 U.S.C. 154(b) by 0 days.

(21) Appl. No.: 15/524,164

(22) PCT Filed: Nov. 4, 2015

(86) PCT No.: PCT/IB2015/002181
§ 371 (c)(1),
(2) Date: May 3, 2017

(87) PCT Pub. No.: WO2016/071756
PCT Pub. Date: May 12, 2016

(65) Prior Publication Data
US 2017/0360894 A1 Dec. 21, 2017

Related U.S. Application Data

(60) Provisional application No. 62/197,286, filed on Jul. 27, 2015, provisional application No. 62/075,144, filed on Nov. 4, 2014.

(51) Int. Cl.
A61K 38/28 (2006.01)
A61K 9/107 (2006.01)
A61K 31/43 (2006.01)
A61K 31/7036 (2006.01)
A61K 45/06 (2006.01)
A61K 33/10 (2006.01)
A61K 33/00 (2006.01)
A61K 38/14 (2006.01)
A61K 31/7068 (2006.01)
A61K 33/08 (2006.01)
A61K 9/00 (2006.01)

(52) U.S. Cl.
CPC ............ *A61K 38/28* (2013.01); *A61K 9/0056* (2013.01); *A61K 9/1075* (2013.01); *A61K 31/43* (2013.01); *A61K 31/7036* (2013.01); *A61K 31/7068* (2013.01); *A61K 33/00* (2013.01); *A61K 33/08* (2013.01); *A61K 33/10* (2013.01); *A61K 38/14* (2013.01); *A61K 45/06* (2013.01)

(58) Field of Classification Search
None
See application file for complete search history.

(56) References Cited

U.S. PATENT DOCUMENTS

| 4,327,076 | A | 4/1982 | Puglia et al. |
| 5,824,638 | A | 10/1998 | Burnside et al. |
| 6,656,701 | B2 | 12/2003 | Bishop et al. |
| 6,919,372 | B1 | 7/2005 | Yamashita et al. |
| 7,018,980 | B2 * | 3/2006 | Zheng .................... A61K 9/107 514/6.5 |
| 8,088,734 | B2 | 1/2012 | Mehta et al. |
| 2003/0022944 | A1 | 1/2003 | Gumkowski et al. |
| 2003/0077297 | A1 | 4/2003 | Chen et al. |
| 2009/0061011 | A1 | 3/2009 | Talton |
| 2009/0104264 | A1 | 4/2009 | Bando et al. |
| 2009/0175959 | A1 * | 7/2009 | Bando ...................... A61K 9/16 424/683 |
| 2009/0176691 | A1 | 7/2009 | Bennis et al. |
| 2010/0273730 | A1 | 10/2010 | Hsu et al. |
| 2011/0293714 | A1 | 12/2011 | Foger |
| 2012/0213855 | A1 | 8/2012 | Agarwal et al. |
| 2014/0127296 | A1 | 5/2014 | Tibbs et al. |

FOREIGN PATENT DOCUMENTS

WO   2011086093 A2   7/2011

OTHER PUBLICATIONS

Ma, Er-li, et al. "In vitro and in vivo evaluation of a novel oral insulin formulation." Acta pharmacologica sinica 27.10 (2006): 1382.*
Written Opinion of the International Searching Authority for PCT/IB2015/002181.
Elsayed, 2012, "Oral Delivery of Insulin: Novel Approaches," In: Recent Advances in Novel Drug Carrier Systems, Demir, Ed., InTech, DOI: 10.5772/52265, pp. 281-314.
Khan et al., 2012, Journal of Pharmacy and Alternative Medicine, 1:13-19.

(Continued)

Primary Examiner — John Pak
Assistant Examiner — Daniel L Branson
(74) Attorney, Agent, or Firm — Birch, Stewart, Kolasch & Birch, LLP

(57) ABSTRACT

The disclosure relates to a dosage forms and combinations of dosage forms useful for effective oral administration of drugs which are otherwise unsuitable for oral administration, owing to acid- and/or protease-mediated degradation. The dosage forms include a self-microemulsifying drug delivery system (SMEDDS) with which the drug is combined and an antacid. When co-administered to a mammal, the dosage form(s) can prevent drug degradation by the strong acid and digestive enzymes normally present in the gastric environment, and can improve water-soluble drug absorption in gastrointestinal (GI) tract. The dosage forms can be used to effectively administer insulin by an oral route, for example, such as in the form of a powder that can be stored for long periods and reconstituted with water or another fluid shortly before administration.

12 Claims, 9 Drawing Sheets

(56) References Cited

OTHER PUBLICATIONS

Ahmad et al., Oral Nano-Insulin Therapy: Current Progress on Nanoparticle-Based Devices for Intestinal Epithelium-Targeted Insulin Delivery, Journal of Nanomedicine & Nanotechnology, vol. S4, No. 01, Jan. 1, 2011.

Akula et al., Self-Microemulsifying Drug Delivery Systems: An Attractive Strategy for Enhanced Therapeutic Profile, International Scholarly Research Notices, vol. 2014, Dec. 8, 2014, pp. 1-11.

G. Fuhrmann et al., In vivo fluorescence imaging of exogenous enzyme activity in the gastrointestinal tract, vol. 108, No. 22, May 16, 2011, pp. 9032-9037.

Sermkaew et al., Development, Characterization and Permeability Assessment Based on Caco-2 Monolayers of Self-Microemulsifying Floating Tablets of Tetrahydrocrcumin, AAPS Pharmscitech, vol. 14, No. 1, Jan. 15, 2013, pp. 321-331.

Supplementary European Search Report for European Patent Office Application No. 15856347.

\* cited by examiner

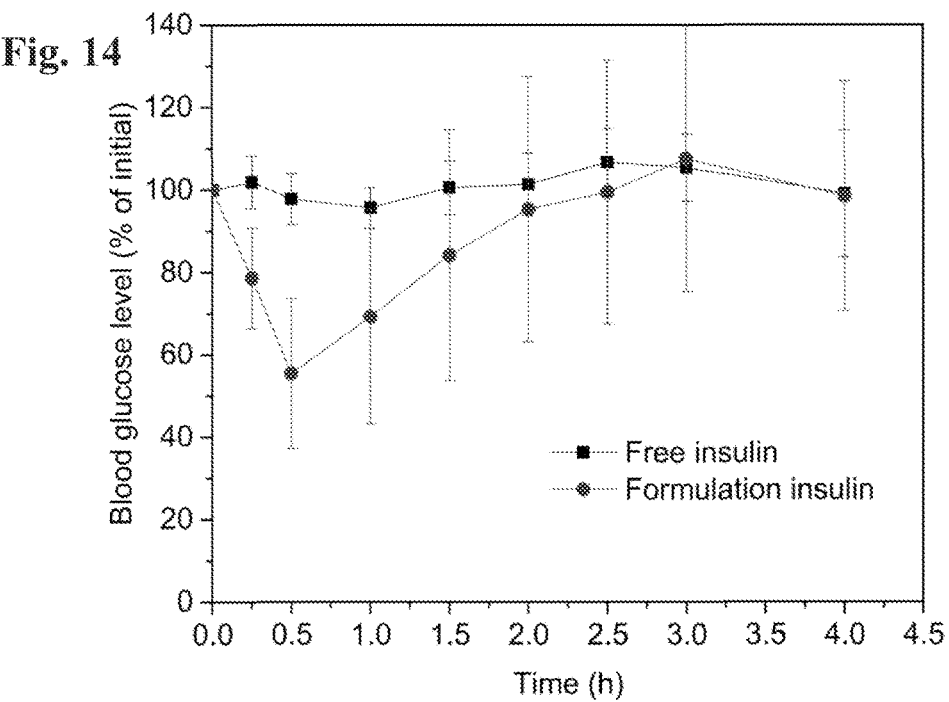
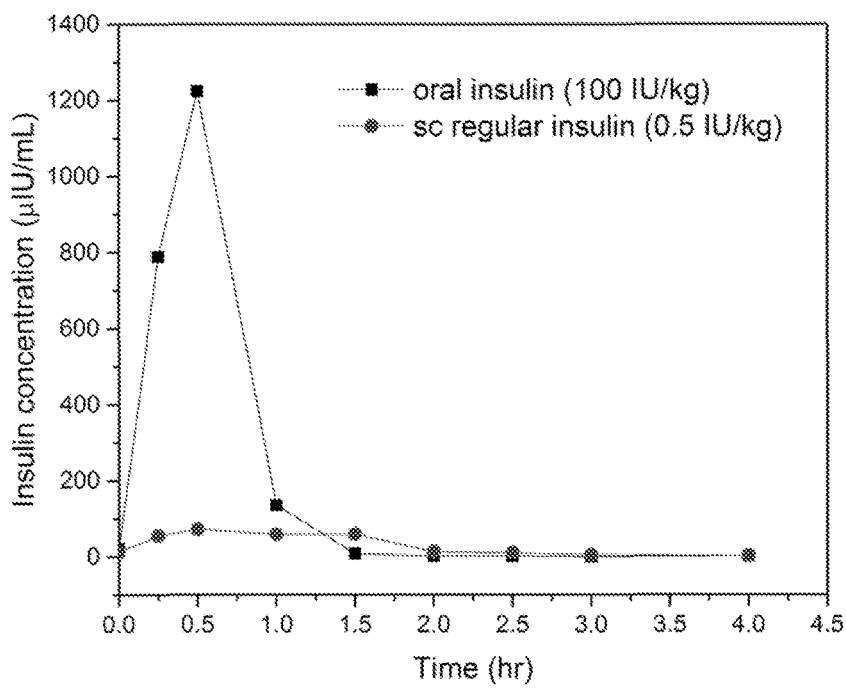

ORAL ADMINISTRATION OF UNSTABLE OR POORLY-ABSORBED DRUGS

CROSS-REFERENCES TO RELATED APPLICATIONS

This application is a national stage application corresponding to international application PCT/IP2015/002181, filed 4 Nov. 2015, which is entitled to priority to U.S. provisional patent application No. 62/075,144 filed 4 Nov. 2014 and to U.S. provisional patent application No. 62/197,286 filed 27 Jul. 2015.

BACKGROUND OF THE DISCLOSURE

The invention relates generally to the field of oral administration of drugs, such as human insulin, that are unstable in the gastrointestinal (GI) tract or poorly absorbed therefrom.

Many drugs are ineffective when orally administered due to instability of the drug in the GI tract and low permeability through GI surfaces. Protein-digesting enzymes such as pepsin and strong acids can further contribute to instability of peptide and protein drugs in the stomach, which can further inhibit stability and efficacy of such drugs. In addition, drugs having low lipophilicity and/or high molecule weight tend to not be easily absorbed through epithelial layers in the GI tract.

Several strategies have been reported to improve stability and bioavailability of orally administered active agents. Specifically, entrapping drugs in carriers such as liposomes, micelles, nanoparticles, water-in-oil (w/o) or water-in-oil-in-water emulsions (w/o/w) or microemulsions, or in enteric-coated capsules have been suggested to shield active compounds from exposure to unfavorable chemical environments (e.g., low pH or digestive enzymes). Such approaches can have drawbacks such as low drug stability, low drug loading, ineffectiveness, complex processing requirements, and high cost.

U.S. Pat. No. 6,191,105 discloses preparation of w/o micro-emulsion formulations of insulin. The w/o emulsion may be unstable due to phase transition that occurs upon oral delivery, with the consequence of exposing drug directly to the harsh GI environment.

U.S. Pat. No. 6,277,413 discloses w/o/w emulsions wherein water-soluble drugs were incorporated into the internal aqueous phase. These emulsions exhibited low drug loading.

U.S. Pat. No. 5,552,156 discloses use of liposomes and micelles as drug carriers. Preparation of such formulations was complex and costly.

Australian Patent 2004305395 discloses nanoparticle compositions of water-soluble drugs for oral administration and preparation. The method of preparing the compositions involves freeze-drying the nanoparticle, which may increase preparation cost.

U.S. patent application Ser. No. 13/561,105 discloses enteric-coated capsules containing cationic nanoparticles to prevent acidic degradation of active substances such as insulin. The process disclosed for making the capsules was complex, including freeze drying and preparation of enteric-coated capsules.

U.S. patent application Ser. No. 13/521,377 discloses compositions for oral administration of insulin peptides using self-microemulsifying drug delivery systems (SMEDDS) in an enteric-coated soft capsule. The insulin peptide in the SMEDDS formulation is still unstable (degraded or inactivated) at acidic environment of stomach. In order to overcome stability, the insulin peptide in SMEDDS is placed in enteric-coated carrier to protect active compounds from cleavage or other degradation in the stomach. However, the enteric-coated carrier exhibits undesirably delayed onset-of-action when orally administered. In addition, gastric emptying time differs among humans, and this will affect the timing of insulin release from the formulation and corresponding absorption through intestines. Such variations induce wide variations in insulin absorption, potentially leading to out-of-control blood sugar levels.

SMEDDS in liquid dosage forms has limitations such as excipient-capsule incompatibility (see, e.g., Mu et al., 2013, Int. J. Pharm. 453(1):215-224 and Kallakunta et al., 2012, Powd. Technol. 221:375-382).

United States patent application publication number 2011/0293714 discloses compositions that include a polar organic solvent and a lipophilic component and that are used for oral administration of derivatized insulin peptides. A high oral dose (840 IU/kg) of such compositions must be used to reduce blood glucose.

United States patent application publication number 2009/0176691 discloses monophasic formulations that include a buffering agent and a protein active agent in a free form. These monophasic formulations are intended to be administered orally, with the buffering agent causing the pH of the stomach and/or intestines to be buffered in the pH range 4-8 following oral administration.

At least some of the technologies described by others yield compositions which effect absorption of drugs (e.g., insulin) following oral administration (e.g., Wong, 2010, J. Drug Target. 18(2):79-92; Arbit et al., 2009, Diabetes Sci. Technol. 3(3):562-567). However, the applicants believe that no oral formulations have been designed which exhibit a rapid onset, high bioavailability and, optionally, short duration of activity, as would be of particular utility for drugs such as insulins. Conventional oral insulin formulations are reported to have a slow onset time (over 1.5 hours) and a long effective duration (over 5 hours). It would be beneficial for medical practitioners and patients to have access rapid-acting (onset within 15 minutes) and short duration (less than 5 hours) of drugs such as insulin in order to provide efficacious metabolic control using a convenient, orally-administered dosage form.

The present disclosure describes compositions which overcome at least some shortcomings of previous compositions, and provide rapidly-acting, short duration drug compositions, even for drugs which are unstable or poorly bioavailable when orally administered using conventional formulations.

BRIEF SUMMARY OF THE DISCLOSURE

The disclosure relates to a dosage form for orally administering a hydrophilic drug to the bloodstream of a mammal. The dosage form includes a bolus of an antacid sufficient to raise the gastric pH of the mammal to at least about 3 (preferably at least about 3.4) upon ingestion of the dosage form (e.g., the bolus can be capable of neutralizing 1-7 milliequivalents of stomach acids). The dosage form also includes a substantially homogenous combination of a therapeutically effective amount of the drug and a surfactant system. The surfactant system includes a non-ionic surfactant.

The identity and amount of the surfactant system are selected to be sufficient to induce spontaneous emulsification upon contact between the combination and an aqueous medium under conditions of mild mechanical agitation, such as conditions that occur in the mammal's stomach or in a container (e.g., a small cup) in which the combination is swirled with a small amount of aqueous medium prior to administration. By way of example, the identity and amount of the surfactant system can be selected to be sufficient to induce spontaneous emulsification upon contact between the combination and a nine-fold excess of distilled water under conditions of mechanical agitation characteristic of the stomach of the mammal. (The precise objective standard selected is not critical; the surfactant system can be selected to be sufficient to induce spontaneous emulsification upon contact with a four- or two-fold excess of distilled water or of USP simulated gastric fluid, for example.) Preferably, the identity and amount of the surfactant system are selected such that the average droplet size of the emulsion formed upon contact between the combination and the aqueous medium is not greater than about 2000 nanometers (or smaller, such as preferably not greater than about 800, 500, or 300 nanometers).

In the dosage form, the bolus can be included in the substantially homogenous combination. Alternatively, the bolus and the combination can be present at distinct portions of the dosage form, such as in the form of distinct solids, powders, or liquids.

The dosage form is useful for administering a variety of hydrophilic drugs, including drugs which are normally poorly bioavailable when administered orally. Examples of such drugs include insulin peptides (e.g., anthrotherapeutic insulins such as isolated or synthesized human insulin peptides), growth hormones, gentamicin, gemcitabine, penicillins, and vancomycin.

The dosage form can be supplied in the form of a kit that includes the dosage form and an amount of the aqueous medium sufficient to dissolve or suspend the bolus of the antacid and to emulsify the combination. Alternatively, it can be supplied in the form of a kit that includes a first dosage form that includes the bolus of antacid and a second dosage form including the substantially homogenous combination of the drug and the surfactant system.

The disclosure further relates to a method of orally administering a hydrophilic drug to the bloodstream of a mammal. The method is performed by combining a therapeutically effective amount of the drug and the surfactant system described herein, mixing the combination, the aqueous medium and a bolus of an antacid sufficient to raise the gastric pH of the mammal to at least about 3 to yield an emulsified mixture; and thereafter orally administering the emulsified mixture to the mammal.

In an alternative method, the drug and the surfactant system are combined to yield a combination, the bolus of antacid is orally administered to the mammal, and the combination is orally administered to the mammal sufficiently closely in time to administration of the bolus that the gastric pH of the mammal remains at least about 3 while the combination is administered.

BRIEF SUMMARY OF THE SEVERAL VIEWS OF THE DRAWINGS

FIG. 14 is a graph of blood glucose levels over time, calculated as a percent of initial blood glucose values, for streptozotocin (STZ)-induced diabetic mice to which were orally administered 200 IU/kg of either a free insulin solution (filled squares) or rapid-acting oral formulation insulin described in an example herein (filled circles).

FIG. 15 is a graph of plasma insulin concentration over time for Beagle dogs to some of which were orally administered 25 IU/kg of insulin in Formulation 8, and to others of which were administered by subcutaneously (SC) injection 0.5 IU/kg free insulin. Data shown are averages and standard deviations for groups of three beagle dogs each.

DETAILED DESCRIPTION

Figure 1:
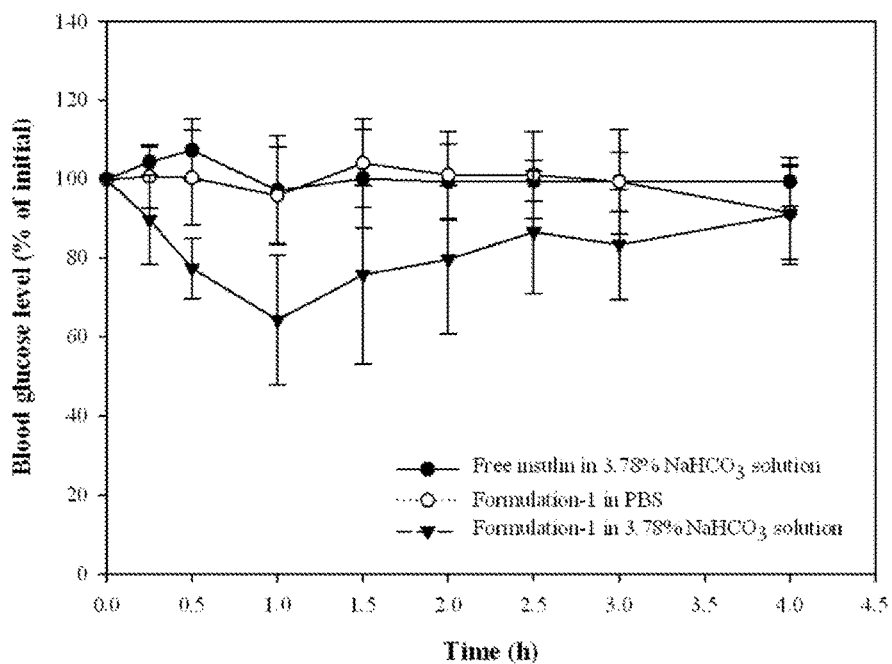
FIG. 1 is a graph of blood glucose levels over time, calculated as a percent of initial blood glucose values, for streptozotocin (STZ)-induced diabetic mice to which were orally administered 200 IU/kg of insulin in a 3.78% (w/v) aqueous solution of sodium bicarbonate ($NaHCO_3$) (filled circles), in phosphate-buffered saline (PBS) (open circles), or in Formulation 1 suspended in a $NaHCO_3$ solution (final concentration 3.78%; triangles). Data shown are averages and standard deviations for groups of 8 mice each.

This disclosure relates to oral formulations and dosage forms for drugs (especially hydrophilic drugs) that are unstable in acidic solutions, that are susceptible to digestion by pepsin or other gastric protease/peptidase, that exhibit low gastrointestinal permeability, that exhibit undesirably delayed onset-of-action when orally administered, that exhibit undesirably long duration-of-action when orally administered, or any combination of these (collectively, "gastrically impractical drugs"). The oral formulations include both i) a self-(micro)emulsifying drug delivery system (SMEDDS) that includes the drug and ii) a bolus of an antacid that is sufficient to raise gastric pH to at least about 3, and preferably to 3.4 or higher, upon oral administration of the formulation to a subject, such as a human or other mammal.

SMEDDS technology is known and understood (see, e.g., Khan et al. 2012, J. Pharmacy Alt. Med. 1:13-19; U.S. Patent Application Publication No. 2003/0022944; U.S. Patent Application Publication No. 2010/0273730). SMEDDS are isotropic mixtures of one or more relatively hydrophobic solvents, one or more surfactants, and drug which exhibit the ability to form fine microemulsions (e.g., micelles or liposomes) upon mild agitation following dilution in (e.g., contact with) an aqueous phase. Enhancing bioavailability of hydrophobic and hydrophilic drugs by incorporating such drugs into SMEDDS formulations has been described by others. However, merely incorporating into a SMEDDS a drug which exhibits undesirable bioavailability or pharmacokinetics when orally administered often does not reliably render bioavailability or pharmacokinetics adequate for pharmaceutical purposes. This is particularly so for drugs which are sensitive (i.e., degraded, cleaved, or inactivated by) to the acidic conditions in the stomach or to the action of one or more proteases or peptidases (e.g., pepsin) that normally occur in the stomach.

Disclosed herein is a formulation that includes both a drug-containing SMEDDS composition and a bolus of an antacid. These two components can be orally co-administered to a mammalian subject (or orally administered to the subject sufficiently closely in time that the antacid effect of the bolus overlaps the period that the drug-containing SMEDDS composition resides in the stomach) to both effectively deliver the drug across the gastrointestinal barrier and reduce or eliminate degradation of the drug by gastric acid and/or enzymes.

The subject matter disclosed herein includes dosage forms for orally administering to a mammal (e.g., a human) a drug (preferably a hydrophilic drug) that is poorly gastroavailable when the drug is orally administered to the mammal in a simple immediate-release form (e.g., a tablet, capsule, collection of granules, or solution). The dosage form includes a bolus of an antacid sufficient to raise the gastric pH of the animal to at least about 3 upon ingestion of the dosage form. The dosage form also includes (either as an additional part of a unitary dosage form or as a companion part of a multi-piece dosage form) a combination (preferably a substantially homogenous combination) of i) a therapeutically effective amount of the drug, ii) optionally, a polyol solvent, and iii) a surfactant system that includes a non-ionic surfactant. A composition is "substantially homogenous" when it is well-mixed or -combined, such that it appears to an ordinary pharmacist to have a visually uniform composition (i.e., even if the composition includes visually distinguishable components, those components appear to be uniformly distributed throughout the composition). The identities and amounts of the drug, any polyol solvent, and the surfactant system are selected so that when the combination is contacted with an aqueous phase under conditions of mild mechanical agitation, the combination spontaneously emulsifies. Thus, for example when the combination is swirled in a cup with water (or another aqueous liquid, such as a beverage) prior to oral administration, or when the combination contacts the aqueous contents of the stomach, the combination emulsifies, yielding a drug-containing emulsion in the GI tract of the mammal. Because the bolus of antacid reduces acidity in the stomach and consequently reduces the activity of gastric proteolytic enzymes, stability of the drug in the emulsion is enhanced and uptake of the drug by the mammal (i.e., into the mammal's bloodstream) is also enhanced.

The formulations described herein can prevent drug degradation in the presence of strong acid and digestive enzymes normally found in the gastric environment of mammals. The formulations can also improve drug absorption in the GI tract. These formulations can enhance the rate of drug uptake and can, optionally, limit the duration of action of the drug (e.g., by including a limited amount of antacid). In the context of some drugs, such as insulin, a rapid onset of action (within 15-30 minutes after administration for insulin, for example) and a relatively short duration of action (falling to less than 25% of maximal activity less than 5 hours, and preferably less than about 4 hours, following administration for insulin, for example) are desirable. Thus, orally-administered insulin-containing formulations described herein can mimic the relative immediacy and short duration of action characteristics of subcutaneously-injected insulin, for example. In other embodiments, the drug can be included in a composition from which the drug will be released over an extended period of time (e.g., from 0-24 hours, such as by selecting formulation components from which the drug transfers to aqueous gastrointestinal fluids only slowly).

Components of the compositions and methods described herein are described below in greater detail.

The compositions described herein for oral administration of drugs which are ordinarily poorly absorbed from the GI tract have two primary components, which may be combined into a unitary dosage form, packaged as a kit including two or more components, or provided separately to a medical practitioner or patient for combined use. The two primary components of the compositions are a "SMEDDS composition" (i.e., a combination of a microemulsion concentrate and a drug that can, optionally, be homogenous) and a bolus of antacid. The bolus of antacid is administered to a mammalian patient such as a human to increase the pH of the stomach (and, optionally, other portions of the GI tract). The SMEDDS composition includes the drug and spontaneously emulsifies upon contact with an aqueous medium to yield droplets (e.g., micelles) which include or contain the drug and which facilitate drug delivery across cell layers (e.g., gastric or small intestinal epithelia) along the GI tract. Drug delivered across these cell layers can enter systemic blood circulation and be delivered throughout the body.

The SMEDDS composition and the antacid bolus components can be administered to a subject in a dosage form in which the two components are combined. By way of examples, they can be administered in a dosage form that includes a liquid in which both components are suspended or dissolved, one that includes separately-powdered forms of the two components that are admixed, or one that includes an adsorbant (e.g., an insoluble mineral powder such as silica particles) on which one or both components are adsorbed. Alternatively, the two components can be administered in a dosage form in which the two components occur in separate locations (e.g., a bilayer tablet or multi-compartment capsule in which the two components occur in separate compartments). As another alternative, the two components can be administered in separate dosage forms, so long as the SMEDDS composition is administered during the period of time in which the antacid bolus causes gastric pH to be above about 3. Compositions in the form of liquids that are prepared prior to oral administration or in the form of powders can, advantageously, be administered to patients having difficulty swallowing tablets or capsules.

The SMEDDS Composition

An important part of the compositions and methods described herein relates to a drug-containing composition that spontaneously emulsifies upon contact with water or an aqueous medium to form droplets which include the drug. Because this disclosure is directed primarily toward enhancing delivery of gastrically impractical drugs (e.g., relatively hydrophilic drugs) such as polypeptides (e.g., anthrotherapeutic insulins), the droplets which are formed are preferably micelles which include the drug or a fraction of the drug. These micelles are suspended in an aqueous medium and the suspension is administered to the subject. Alternatively, the micelles can be formed in the GI tract by administering the SMEDDS composition, optionally (i.e., in case the stomach contains relatively little fluid) together with sufficient aqueous liquid (e.g., the antacid bolus dissolved in water) to facilitate emulsification in the stomach. In the GI tract of the subject, the micelles facilitate transit of the drug across GI cell layers, preferably into the bloodstream of the subject, whence they can be carried to a desired site of action (e.g., within the blood or thence to a body location distant from the GI tract).

The SMEDDS composition is a combination of a therapeutically effective amount of the drug to be administered and a surfactant system. The drug can be dissolved or suspended in an aqueous solution, a polyol solvent, or both prior to combining it with the surfactant system. The drug can also, for example, be combined with the surfactant system in a powdered (e.g., anhydrous or hydrated powder) form. The surfactant system includes a non-ionic surfactant. The identity and amount of surfactant system are selected such that the SMEDDS combination spontaneously emulsifies upon contacting an aqueous medium under conditions of mild mechanical agitation, such as the SMEDDS composition being gently swirled in a container (e.g., a beverage glass or unit dosage cup) following its combination with the medium. In one embodiment, the SMEDDS composition is kept discrete (e.g., in the form of a powdered or granulated composition contained within a capsule that is swallowed whole and that subsequently dissolves within the GI tract) until just before or after it is swallowed by a subject, and the SMEDDS composition emulsifies within the gastrointestinal (GI) tract of the subject when it contacts aqueous fluid therein (e.g., in the form of a powdered or granulated composition contained within a capsule that is swallowed whole and that subsequently dissolves within the stomach or small intestine). The timing of combining the drug and the surfactant system is not critical. Where stability concerns permit, the drug can be admixed (e.g., homogenously) with the surfactant system; alternatively, the drug and surfactant system can be combined (e.g., by mixing a powdered drug with a liquid surfactant system) immediately before or simultaneously with combining the two with the antacid bolus.

The SMEDDS composition can also include a polyol solvent, such as glycerol, propylene glycol, or a polyethylene glycol (or other polyether compound) that is liquid in its pure state at 20 degrees Celsius and atmospheric pressure. The polyol solvent can function to aid combination of the drug with the surfactant system, coating of the combined drug/polyol/surfactant system onto an adsorbant, or dissolution of the drug into the aqueous medium, for example. The quantity of the polyol that is included within the SMEDDS composition is not critical and can be readily empirically determined by an artisan in this field, depending on the intended purpose(s) of the polyol. By way of example, the SMEDDS composition can include from about 0-80% by weight polyol prior to combination with the aqueous medium. In formulations which include human insulin as the drug, SMEDDS compositions which include at least about 40% by weight polyol are desirable.

An important characteristic of the SMEDDS composition is that at least some droplets formed upon contact between it and an aqueous medium have a size that is appropriate for transit through or across cell layers of the GI tract. The droplets should have a size (i.e., diameter) not greater than about 500 nanometers, preferably not greater than about 300 nanometers, and preferably have a size of at least about 10 nanometers. The size of the droplets that are formed is determined by the composition of the SMEDDS composition, primarily by the surfactant system.

Formulation of self-emulsifying compositions is known in the art (see, e.g., Khan et al. 2012, J. Pharmacy Alt. Med. 1:13-19; U.S. Patent Application Publication No. 2003/0022944; U.S. Patent Application Publication No. 2010/0273730; and others). Inherent in formulation of self-emulsifying compositions having selected droplet size distributions are routine trials of multiple combinations and proportions of ingredients, such as the identities and concentrations of surfactants used. Some degree of empirical testing is routinely performed in selecting the identities and concentrations of components used.

The SMEDDS composition may be prepared, packaged, and/or administered to a subject as a substantially homogenous composition, being either a substantially homogenous monophasic liquid, a substantially uniform powder or granulation (e.g., loose, compacted into a tablet, or contained within a capsule), or a substantially homogenous emulsion (e.g., a w/o emulsion, or a w/o/w emulsion). When in the form of an emulsion, the SMEDDS composition preferably contains the drug in the dispersed aqueous phase of the emulsion (i.e., within the water phase of a w/o emulsion). In one embodiment, the SMEDDS composition is prepared, packaged, and/or administered in the form of a powdered or granulated mixture (optionally including the antacid bolus) that is intended to be mixed with water or another aqueous fluid (to facilitate emulsification of the SMEDDS composition) shortly (within 24 hours, preferably within 2 hours) or immediately before oral administration.

The SMEDDS composition is useful for enhancing delivery of drugs across gastric and intestinal membranes, such as through the tight junctions known to exist between intestinal epithelial cells. The compositions can be used to enhance delivery of drugs of substantially any hydrophilicity/hydrophobicity, but this disclosure focuses particularly on relatively hydrophilic drugs, which are ordinarily subjected to acids and enzymes which are contained in the aqueous medium of mammalian gastric fluids. Examples of such drugs include insulin peptides, growth hormones, erythropoietin, antibodies (e.g., monoclonal antibodies) and antibody fragments, gentamicin, gemcitabine, penicillins, and vancomycin.

Insulin peptides represent a particularly important class of drugs which are known to be susceptible to degradation and/or inactivation in gastric fluids. The family of gastric proteases referred to generically pepsin is known to cleave insulin peptides at defined sites under acidic (pH<3.4) conditions which occur normally in mammalian stomachs. Pepsin has maximal activity at about pH 2.0 and is substantially inactive at pH 6.5 or higher. Thus, the antacid bolus can be selected to yield a gastric pH greater than about 3, preferably greater than 3.4, and more preferably even higher (there may be negligible additional benefit in inducing gastric pH>6.5). Insulin peptides are also known to be subject to deamidation under acidic conditions. Cleaved and/or deaminated insulin peptides exhibit less of the beneficial pharmaceutical activity of intact insulin, which likely accounts for the inefficacy of insulin for treatment of insulin-responsive disorders (e.g., diabetes) when insulin is administered by an oral route. The compositions described herein protect insulin (and other drugs) from the inactivating effects of stomach acid and proteases and also facilitates insulin transit across GI membranes. The compositions and methods described herein therefore have particular utility in enhancing the bioavailability of insulin peptides when they are administered by an oral route.

Numerous insulin peptides are known, and this term is used herein to refer both to naturally-occurring forms of insulin (e.g., ordinary, non-modified human insulin) and synthetic insulins and insulin-like peptides (e.g., those generated by modification of naturally-occurring insulin or through non-biotic synthetic routes). The precise identity of the insulin peptide is not critical. Preferably, the insulin peptide is an anthrotherapeutic insulin, in that it induces one or more physiological effects in a human to whom it is administered that are similar or identical to those induced by injection (e.g., intravenous, intramuscular, or subcutaneous) of naturally-occurring human insulin.

The amounts of the drug and any polyol or aqueous solvents that are incorporated into the SMEDDS composition are not critical, so long as the SMEDDS composition retains its ability to spontaneously emulsify upon contact with an excess of aqueous fluid. The SMEDDS composition should include at least enough of the drug to have a desired pharmaceutical effect on a subject when a unit dose of the SMEDDS composition is administered to the subject. The aqueous solution should be selected to be compatible with (i.e., not cause significant degradation or inactivation of) the drug during the period and under the conditions of anticipated storage between manufacture and administration of the SMEDDS composition. Appropriate amounts of the aqueous solution can improve processability of the SMEDDS composition during its manufacture and will typically not exceed about 30% (w/w) of the SMEDDS composition, and preferable make up 20%, 10%, or less of the SMEDDS composition. The SMEDDS composition can be made in bulk and dispensed in aliquots into unit dosage forms appropriate for administration to individual subjects; in such instances, the bulk SMEDDS composition will include multiples of an effective dose of the drug, while each unit dose will include a single effective dose. By way of example, a bulk SMEDDS composition may be prepared and packaged into one compartment of numerous dual-compartment individual dosage forms (e.g., capsules).

The SMEDDS composition can include a polyol solvent, such as one or more of glycerol, propylene glycol, and polyethylene glycols (PEG). Other similar compounds (e.g., other polyethers) can likewise be used. Polyol solvents can facilitate dissolution or suspension of drugs (e.g., insulin) in the other components of the SMEDDS composition, thereby enhancing the drug-uptake-inducing effect of the SMEDDS composition. When a polyol solvent is included, the SMEDDS composition preferably includes at least about 5% (w/w) of the polyol solvent(s), and preferably not more than about 50% (w/w). In some SMEDDS compositions appropriate polyol(s) content of the composition is in the range from about 20-30% (w/w) of the composition.

The SMEDDS composition includes a surfactant system that, in combination with the drug and any included aqueous or polyol solvent, renders the SMEDDS composition spontaneously-emulsifying upon contact with an aqueous medium. No precise degree or speed of emulsification is required, but it is preferable that substantially all of the SMEDDS composition emulsifies within one hour when it is combined with a nine-fold excess of distilled water at 20 degrees Celsius under gentle stirring (i.e., nine parts water and one part SMEDDS composition stirred in a temperature-controlled beaker with a stir bar rotating at 10 rotations per minute). The surfactant system includes at least one non-ionic surfactant, and preferably includes at least one surfactant selected from the group consisting of polyglycolyzed glycerides having at least one acyl moiety and propylene glycol esters of fatty acids. A polyglycolyzed glyceride as used herein refers to a mixture of monoglycerides, diglycerides and triglycerides with mono-fatty acid esters and/or di-fatty acid esters polyethylene glycol (PEG), having Hydrophilic Lipophilic Balance (HLB) values of between and including 4 and 19 (preferably from 6 to 14). The acyl moiety(ies) is a straight- or branched-chain alkane or alkene (preferably having not more than two alkenyl bonds) compound including from 8 to 18 carbon atoms. Preferred acyl moieties include —CO—$(CH_2)_7CH_3$, —CO—$(CH_2)_9CH_3$, —CO—$(CH_2)_{11}CH_3$, —CO—$(CH_2)_{13}CH_3$, —CO—$(CH_2)_7$—CH=CH—$(CH_2)_7CH_3$, and —CO—$(CH_2)_7$—CH=CH—$CH_2$—CH=CH—$(CH_2)_4CH_3$. Examples of polyglycolyzed glycerides include oleoyl polyoxylglycerides (oleoyl polyoxyl-6 glycerides such as Labrafil® M-1944CS), linoleoyl polyoxylglycerides (linoleoyl polyoxyl-6 glycerides such as Labrafil® M-2125CS), caprylocaproyl polyoxylglycerides (PEG-6 caprylic/capric glycerides such as SOFTIGEN® 767), caprylocaproyl polyoxyl-8 glycerides (e.g., Labrasol®), lauroyl polyoxylglycerides (Gelucire® 44/14), and combinations of these.

Propylene glycol esters of fatty acids, as used herein, refer to a mixture of propylene glycol mono- and diesters of saturated and unsaturated fatty acids, preferably derived from edible oils and fats, which can be produced either by direct esterification of propylene glycol with fatty acids or by transesterification of propylene glycol with oils or fats. When prepared by transesterification, the product may contain residual mono- and diglycerides and glycerol, which process may be followed by molecular distillation to separate the monoesters. Examples of propylene glycol esters of fatty acids include propylene glycol monocaprylate, propylene glycol dilaurate, propylene glycol monolaurate, propylene glycol dicaprylocaprate, propylene glycol laurate, propylene glycol caprylate.

The surfactant system can further include an additional surfactant (or more than one), such as one selected from the group consisting of polysorbate, poloxamers, polyoxyethylene castor oil derivatives, polyoxyethylene alkyl ethers, sorbitan fatty acid esters, glyceryl monooleate, glyceryl monolinoleate, medium-chain triglycerides, polyglyceryl oleate, lauroyl polyoxylglyceride, stearoyl polyoxylglycerides, and combinations of these.

Formulation of self-emulsifying compositions is known in the art, including selection of the identity(ies) and concentration of surfactant(s) included in such compositions. The identity and concentration of the surfactant(s) included in the surfactant system are not critical, other than that they are selected such that they confer to the SMEDDS composition the ability to spontaneously emulsify upon contact with an aqueous medium (optionally, with mild agitation). Preferably, the surfactant system makes up about 5-90% (w/w) of the SMEDDS composition, more preferably, at least about 20%, at least about 30%, at least about 40%, at least about 50%, and still more preferably at least about 60% (e.g., 20-70%, 40-70%, or 50-70% w/w). As is known in the art, combinations of surfactants are suitable for conferring spontaneous emulsification capacity to drug-containing formulations, and such combinations are appropriate for the surfactant system described herein. Combinations of surfactants can be selected, for example, with reference to their hydrophilic-lipophilic balance (HLB) value (see, e.g., U.S. Patent Application Publication Nos. 2003/0022944 and 2010/0273730). When HLB values are used to select a surfactant system, HLB values in the range from about 8 to 19 are considered appropriate for the compositions described herein.

The SMEDDS composition can be made by combining its components in any order that is effective to yield a composition that spontaneously emulsifies upon contacting an aqueous medium. In one appropriate method, the drug is dissolved or suspended in an aqueous solution, and this solution/suspension is thereafter combined with a polyol solvent(s) to form a substantially homogenous uniphasic mixture. The surfactant(s) of the surfactant system are added (individually or after prior combination of surfactants) to this mixture. Depending on the surfactant system selected, gentle stirring, shaking, or other agitation can yield either a second substantially homogenous uniphasic mixture (e.g., if little or no aqueous or polyol solvent(s) are included) or a multiphasic mixture, such as a w/o emulsion or a w/o/w emulsion (especially if relatively large amounts of aqueous solvent(s) are included).

The SMEDDS composition can be associated with an adsorbant. Adsorbants are solid compositions, most often employed in the form of fine powders which act primarily as excipients to facilitate handling of compositions of the drug compositions described herein. Because adsorbants tend to be free-flowing powders or other easily-handled substances, binding, adsorbing, drying, or adhering a component to, upon, or within an adsorbant facilitates handling of that component. Use of adsorbants is well known in the pharmaceutical arts. Examples of suitable adsorbants include silica (e.g., silica powders such as fumed silica) and other mineral powders that are substantially insoluble in water, celluloses (e.g., microcrystalline cellulose powders), and starches.

By way of example, the SMEDDS composition (including the drug) can be solidified upon microcrystalline cellulose granules (e.g., by contacting the granules with a SMEDDS composition including a volatile solvent and thereafter evaporating some or all of the solvent), and the SMEDDS-composition-coated granules can be combined with a powdered antacid to yield the dosage form. Alternatively, the antacid can also be solidified upon the granules (e.g., as an outer layer). As still another alternative, the SMEDDS composition (not yet including the drug) can be coated onto the granules, and them powdered drug and powdered antacid can both be mixed with the granules. A skilled artisan in this field appreciates that many known conformations of adsorbants and the other components of the drug compositions described herein can be employed without departing from the subject matter described herein.

The SMEDDS composition can be stored (preferably at a controlled temperature, such as less than 20 degrees Celsius and preferably above the freezing point of any aqueous phase present therein, such as at 4-5 degrees Celsius) as a substantially homogenous mixture (whether emulsified or not) or it can be combined with an aqueous medium (e.g., water or an aqueous solution/suspension of an antacid) to form an emulsion prior to storage. Dried or low-moisture compositions are known to exhibit superior storage properties under a wide range of conditions. Dosage forms described herein in which one or more components are present in the form of a dry powder (e.g., coating or adhered to an adsorbant) can thus endure more stringent storage conditions, such as storage at a controlled temperature (e.g., less than 30 degrees Celsius and above 0 degrees Celsius) for extended periods.

The SMEDDS composition can be administered directly to a subject (i.e., so that the it will spontaneously emulsify upon contacting the aqueous stomach fluid of the subject) or it can be contacted with an aqueous medium (e.g., a glass of water, a glass of water in which the antacid bolus described herein has been dissolved, or a flavored beverage) prior to administration of the medium to the subject (i.e., so that the SMEDDS composition will fully or partially emulsify in the medium prior to its administration to the subject).

The Antacid Bolus

The compositions and methods described herein involve a bolus of one or more antacids that is sufficient to raise the gastric pH of the animal to which the bolus is administered to at least about 3 upon (i.e., preferably not later than 3-5 minutes after) oral administration of the bolus. The identity of the antacid is not critical, and suitable examples include sodium bicarbonate, magnesium hydroxide, calcium carbonate, and aluminum hydroxide. Other suitable antacids are described in U.S. Patent Application Publication No. 2014/0127296, for example. In an alternative embodiment, the antacid is supplied in a form that is not released as a single bolus upon oral administration, but instead releases antacid over an extended period of time (e.g., 2-24 hours) following oral administration. Extended release antacid preparations are known.

Selection of an appropriate antacid (or combination of antacids) and appropriate amounts of the same to achieve a gastric pH not less than about 3 (preferably not less than 3.4) is within the ken of an ordinary artisan in this field, and takes into account the quantity of acid expected to be present in the stomach of a subject. By way of example, a normal, fasting human is ordinarily expected to have about 1-7 milliequivalents (mEq) of stomach acids within his or her stomach. A skilled artisan in this field is able to calculate amounts of antacids needed to achieve a desired pH in the stomach of a subject for a desired period of time.

The form in which the antacid bolus is packaged and/or administered to a subject is not critical. Liquids are relatively bulky and present difficulties for packaging and storage, but are relatively simple to administer. Solids are more compact and generally shelf-stable, but require hydration and dissolution either prior to administration or within the patient after administration.

The amount of antacid in the bolus will affect the duration for which gastric pH is raised above 3. Generally speaking, greater amounts of antacid will result in a longer duration, at least to a point. Where a relatively short duration of action is desired for the drug, including in the dosage form only enough antacid to raise gastric pH for the desired period of time can serve to limit the duration of action of the drug by permitting gastric secretions which overwhelm the pH-raising effect of the antacid to degrade or inactivate the drug.

A pharmaceutical agent effective to reduce gastric acid secretion can be administered with (or overlapping in time with) the compositions described herein if extended protection of the drug from the effects of stomach acid is desired.

The Dosage Form

The precise form or nature of the dosage form in which the compositions described herein are administered to a subject are not critical. Any of a wide variety of known dosage forms can be used, including tablets, capsules, liquid carriers, and multi-layer or multi-compartment dosage forms. Other contemplated dosage forms include powders, granules, and dosage cups having solid material contained or attached therein, each of which can be combined with an aqueous fluid prior to administration in order to emulsify the SMEDDS composition, suspend or dissolve the antacid, or both. What is important is that the drug be released from the dosage form that contains the SMEDDS composition during a period of time that overlaps the period of time for which the antacid bolus raises gastric pH above about 3.

In one embodiment, the compositions described herein are packaged as powdered unit dosage forms in which a unit dose of solid SMEDDS composition (e.g., powdered SMEDDS composition or an adsorbant having the SMEDDS compositions adsorbed thereto or dried thereon) is combined with unit dosages of the drug (in solid form) and the antacid (also in solid form). The solid components of the dosage form are combined with an aliquot of aqueous fluid (either provided by the subject or included separately with the solid dosage form) in order to form a dispersion, emulsion, or (preferably) nanoemulsion suspended in the aqueous fluid prior to administering the suspension to a patient.

In another embodiment, the compositions described herein are packaged as unit dose forms in which a unit dose of the SMEDDS composition has been emulsified by contacting it with an aqueous medium in which a unit dose of the antacid bolus has been dissolved; the emulsion is administered orally to the subject (e.g., by pouring or squeezing the contents of the unit dosage form into the mouth of the subject or by the subject swallowing the entire dosage form, such as in the form of a capsule).

In another embodiment, the compositions are used by medical practitioners and/or patients in the form of a kit that contains the unit dose of the antacid packaged separately (e.g., as a tablet or liquid) from the unit dose of the SMEDDS composition (e.g., provided within a capsule); the entire dosage form is administered to the patient by administering both the unit dose of the antacid and the unit dose of the SMEDDS composition to the patient.

In yet another embodiment, the unit dose of the antacid and the unit dose of the SMEDDS composition are packaged in separate compartments or layers of a single dosage form (e.g., a multi-compartment container, a coated or bi-layer tablet, or a coated or multi-compartment capsule), so that ingestion of the entire dosage form by a subject will lead to release of the antacid bolus from its compartment (i.e., thereby raising gastric pH to >3) and release of the SMEDDS composition from its compartment (leading to release or formation of a drug-containing emulsion in the GI tract).

In yet another embodiment, the drug and antacid are combined and prepared in the form of a tablet or powder and provided to the patient together with a SMEDDS composition that has already been combined with an aqueous fluid (i.e., so that it is in the form of a suspended nano- or micro-emulsion). In this embodiment, the dosage form is administered to a patient by combining (or having the patient combine) the tablet or powder with the suspended emulsion (to dissolve or suspend the drug and antacid therein) and administering the resulting liquid to the patient.

In still another configurations, the dosage form can be a capsule which contains the SMEDDS composition and which is coated with a rapidly-dissolving antacid bolus. The dosage form can be dropped into a glass of water to form an antacid solution (optionally flavored), and this solution can be used either as a medium to facilitate swallowing of the capsule by the subject or as a medium in which the capsule dissolves (thereby forming a drug-containing emulsion in the medium) and the medium is thereafter consumed by the subject.

This list of exemplary embodiments is not limiting. Substantially any dosage form or method for orally administering two compositions to the same subject can be employed. Administration of the SMEDDS composition should, however, be effected during a period whereby contact between the SMEDDS composition and gastric fluids occurs while gastric pH has been raised above about 3 by administration of the antacid bolus.

Use of the Compositions

The compositions described herein can be used to orally administer a gastrically impractical drug (i.e., a poorly gastroavailable drug such as a hydrophilic drug) to the bloodstream of a mammal. To achieve this, a therapeutically effective amount of the drug is dissolved or suspended in water or an aqueous solution. The dissolved or suspended drug is combined with the surfactant system described herein and, optionally, a polyol solvent. These components are gently mixed to form a substantially homogenous SMEDDS composition, which can be a substantially uniphasic liquid, a w/o emulsion (hydrophilic drugs tending to localize to the water phase), or a w/o/w emulsion (hydrophilic drugs tending to localize to one or both water phases). In another embodiment, the drug is combined with a surfactant system and an adsorbant to form a mixture in a solid form (e.g., a solid granule or powder) that is combined with an aqueous liquid (e.g., water or a suspension of the antacid bolus) prior to administration.

As described herein, the identities and amounts of the drug, any aqueous solvent, any polyol solvent, and the surfactant system are selected such that the SMEDDS composition spontaneously emulsifies upon contacting an aqueous medium under conditions of mild mechanical agitation. The SMEDDS composition is contacted with such an aqueous medium in order to create an emulsion (or to dilute the existing emulsion in the SMEDDS composition), and this emulsion can, optionally, be stored at reduced temperature (preferably above the freezing point of the water phases of the emulsion). The emulsion thus formed is orally administered to a mammal, together with (i.e., shortly before, shortly after, or simultaneously with administration of) a bolus of an antacid sufficient to raise the gastric pH of the animal to at least about 3 (and preferably above 3.4).

Optionally, the emulsion can be formed in the stomach of the subject by administering to the subject a dosage form that releases the SMEDDS composition directly into the stomach. If not already in the form of an emulsion in the dosage form, the SMEDDS composition can spontaneously form an emulsion in the gastric fluids of the subject. Ingestion of water with the dosage form can enhance the likelihood that the gastric contents of the subject include sufficient water to form an emulsion.

The SMEDDS composition should be orally administering to the mammal sufficiently closely in time to administration of the bolus that the gastric pH of the animal remains at least about 3 while the emulsion formed from the SMEDDS composition remains in the stomach of the mammal.

Diabetes and other disorders treatable by administration of insulin peptides to a subject are disorders for which the compositions and methods described herein are considered particularly suitable. Effective acute treatment of insulin-responsive disorders can require a quick onset of action after an insulin peptide is administered, and it can be desirable that the duration of action of the insulin peptide not endure beyond a few hours. For these reasons, injectable compositions of insulin peptides are commonly employed, because insulin peptides tend to be poorly bioavailable (if at all bioavailable at all) when they are administered by other (e.g., oral) routes. As the discussion and examples herein indicate, insulin peptides which are administered orally in one of the formulations described herein can exert a very rapid (<30 minute) onset of action and a duration of action that endures for 2-4 hours. For these reasons, formulations described herein can be used either to deliver insulin peptides on a regular basis or an acute, as-needed basis to subjects in need of insulin therapy. The ability of subjects to ingest the formulations orally, rather than by injection, can also improve the comfort and ease of administration, encouraging patient compliance with prescribed dosing regimes or emergency instructions.

EXAMPLES

The subject matter of this disclosure is now described with reference to the following Examples. These Examples are provided for the purpose of illustration only, and the subject matter is not limited to these Examples, but rather encompasses all variations which are evident as a result of the teaching provided herein.

Example 1

Formulations

Described in this Example are formulations containing insulin

Each of Formulations 1, 2, and 3 was prepared as follows.

Non-modified human insulin (28.8 IU/mg) was weighed into a 7 milliliter vial and the indicated quantity of 0.05 normal HCl was added to the vial to dissolve the insulin. A polyol solvent (propylene glycol, glycerol, and/or PEG 400) was added to the vial and the contents were gently stirred to combine the ingredients. Three surfactants were then added to the vial and the contents were gently stirred until a transparent mixture formed. This transparent mixture was suspended in about 160-230 microliteres of a 3.78% (w/w) NaHCO$_3$ solution (a ten-fold dilution), causing emulsification, prior to administration.

The formulation herein designated Formulation 1 had the following composition:

| Ingredient | Fraction % (w/w) |
|---|---|
| Insulin | 0.85 |
| 0.05N HCl | 12.76 |
| Propylene glycol | 29.78 |
| Labrasol ™ | 51.06 |
| Lauroglycol ™ FCC | 4.26 |
| Tween ™ 80 | 1.29 |

The formulation herein designated Formulation 2 had the following composition:

| Ingredient | Fraction % (w/w) |
|---|---|
| Insulin | 0.80 |
| 0.05N HCl | 17.67 |
| Propylene glycol | 28.11 |
| Softigen ™ 767 | 48.19 |
| Lauroglycol ™ FCC | 4.02 |
| Tween ™ 80 | 1.20 |

The formulation herein designated Formulation 3 had the following composition:

| Ingredient | Fraction % (w/w) |
|---|---|
| Insulin | 0.80 |
| 0.05N HCl | 11.95 |
| Glycerol | 5.95 |
| PEG-400 | 13.90 |
| Tween ™ 80 | 31.70 |
| Cremophor ™ RH40 | 11.90 |
| Labrafil 1944CS | 23.80 |

Labrasol™ is a trademark of Gattefosse USA and is a mixture of PEG-8 caprylic/capric glycerides having the general formula R—(CH$_2$—CH$_2$O)$_8$—R, wherein each —R is either —CO—(CH$_2$)$_6$—CH$_3$ or —CO—(CH$_2$)$_8$—CH$_3$. Lauroglycol™ FCC is a trademark of Gattefosse USA and is a propylene glycol monolaurate (C$_{15}$H$_{30}$O$_3$). Tween™ 80 is a trademark of Sigma-Aldrich Chemical Company and is a mixture of polyoxyethylene (20) sorbitan monooleates. Softigen™ 767 is a trademark of Sasol Olefins & Surfactants GmbH and is a mixture of PEG-6 Caprylic/Capric Glycerides having the general formula R—(CH$_2$—CH$_2$O)$_6$—R, wherein each —R is either —CO—(CH$_2$)$_6$—CH$_3$ or —CO—(CH$_2$)$_8$—CH$_3$. Cremophor™ RH40 is a trademark of BASF Group and hydrogenated castor oil surfactants. The main constituent of Cremophor™ RH 40 is glycerol polyethylene glycol hydroxystearate, which, together with fatty acid glycerol polyglycol esters, forms the hydrophobic part of the product. The hydrophilic part consists of polyethylene glycols and glycerol ethoxylate, having formula is $C_{57}H_{110}O_9(CH_2CH_2O)_n$. Labrafil™ 1944CS is a trademark of Gattefosse USA and has the general structure HO—$(CH_2$—$CH_2O)_6$—CO—$(CH_2)_7$—CH=CH—$(CH_2)_7$—$CH_3$.

Surfactants also considered acceptable but not used in these experiments include Labrafil™ M-2125CS, which is a trademark of Gattefosse USA and has the general structure HO—$(CH_2$—$CH_2O)_6$—CO—$(CH_2)_7$—CH=CH—$CH_2$—CH=CH—$(CH_2)_4$—$CH_3$, and Gelucire 44/41, which is a trademark of Gattefosse USA and has the general formula R—$(CH_2$—$CH_2O)_{32}$—R, wherein each —R is either —CO—$(CH_2)_{10}$—$CH_3$ or —CO—$(CH_2)_{12}$—$CH_3$.

Formulation 4 was prepared by mixing, in a 20 milliliter beaker, 8 milligrams of non-modified human insulin, 300 milligrams of sodium bicarbonte, 100 milligrams of glycerol, and 600 milligrams of Labrasol™. Thereafter, 8992 milligrams of water was added to the beaker and the combined ingredients were mixed by gentle stirring until a nanoemulsion formed.

The formulation herein designated Formulation 4 had the following composition:

| Ingredient | Quantity (mg) | Fraction % (w/w) |
|---|---|---|
| Insulin | 8 | 0.08 |
| Sodium bicarbonate | 300 | 3 |
| Glycerol | 100 | 1 |
| Labrasol | 600 | 6 |
| Water | 8992 | 89.92 |
| Total | 10000 | 100.0 |

Formulation 5 was prepared as follows. In a 20 milliliter beaker, 8 milligrams of insulin, 800 milligrams of sodium bicarbonate, 100 milligrams of glycerol, and 600 milligrams of Labrasol™ were combined and mixed. 8492 Milligrams of water was added to the beaker, and the contents mixed by gentle stirring until a nanoemulsion formed.

The formulation herein designated Formulation 5 had the following composition:

| Ingredient | Quantity (mg) | Fraction % (w/w) |
|---|---|---|
| Insulin | 8 | 0.08 |
| Sodium bicarbonate | 800 | 8 |
| Glycerol | 100 | 1 |
| Labrasol | 600 | 6 |
| Water | 8492 | 84.92 |
| Total | 10000 | 100.0 |

Formulation 6 was prepared as follows. In a 20 milliliter beaker, 8 milligrams of insulin, 210 milligrams of sodium bicarbonate, 90 milligrams of magnesium hydroxide, 100 milligrams of glycerol, and 600 milligrams of Labrasol™ were combined and mixed. Thereafter, 8992 milligrams of water was added to the beaker, and the contents were mixed by gentle stirring until a nanoemulsion formed.

The formulation herein designated Formulation 6 had the following composition:

| Ingredient | Quantity (mg) | Fraction % (w/w) |
|---|---|---|
| Insulin | 8 | 0.08 |
| Sodium bicarbonate | 210 | 2.1 |
| Magnesium hydroxide | 90 | 0.9 |
| Glycerol | 100 | 1 |
| Labrasol | 600 | 6 |
| Water | 8992 | 89.92 |
| Total | 10000 | 100.0 |

Formulation 7 (a powder intended for oral administration after forming a suspension from the powder) was prepared by Adding Labrasol™ drop-wise to Aerosil™ 200 contained in a mortar. After addition, this mixture was homogenized using a corresponding pestle to ensure uniform distribution. Insulin and sodium bicarbonate powder were thereafter added to the Labrasol™-Aerosil™ 200 mixture and the resulting combination was mixed. The resulting powder was passed through a no. 16 sieve (1.19 millimeter nominal sieve opening), dried at ambient temperature, and stored until further use. Thereafter, 1.158 gram of the stored powder was combined with 9 milliliters of water prior to administration, yielding a water-based dispersion.

The formulation herein designated Formulation 7 had the following composition:

| Ingredient | Quantity (mg) | Fraction % (w/w) |
|---|---|---|
| Labrasol ® | 600 | 51.8 |
| Aerosil ® 200 | 250 | 21.6 |
| Sodium bicarbonate | 300 | 25.9 |
| Insulin | 8 | 0.7 |
| Total | 1158 | 100.0 |

Formulation 8 (a powder intended for oral administration after forming an aqueous suspension from the powder) was prepared by Adding liquid Labrasol® drop wise to Neusilin® US2 (a granulated magnesium aluminometasilicate product sold by Fuji Chemical Industry Co., Ltd. having a mean particle size of about 60-120 micrometers) contained in mortar. After addition, the mixture was homogenized using a corresponding pestle to ensure uniform distribution of formulation. Insulin and sodium bicarbonate powders were thereafter added to the Labrasol-Neusilin® US2 mixture and the resulting combination was mixed. The resulting powder was passed through a no. 16 sieve, dried at ambient temperature, and stored until further use. Thereafter, 1.108 gram of this powder was combined with 9 milliliters of water prior to administration, yielding a water-based dispersion.

The formulation herein designated Formulation 8 had the following composition:

| Ingredient | Quantity (mg) | Fraction % (w/w) |
|---|---|---|
| Labrasol ® | 600 | 54.2 |
| Neusilin ® US2 | 200 | 18.0 |
| Sodium bicarbonate | 300 | 27.1 |
| Insulin | 8 | 0.7 |
| Total | 1108 | 100.0 |

Formulation 9 (a two-part formulation) was prepared as follows:

Part A Components:

| Components | weight |
|---|---|
| Mannitol | 277.5 mg |
| Povidone K-30 | 7.5 mg |
| NaHCO$_3$ | 300 mg |
| Insulin | 8 mg |

Part A (granules) was prepared by a wet granulation method, in which all the Part A components were weighed and passed through a #20 sieve. Insulin was dissolved in 0.05 N HCl, and then placed into mortar containing the other Part A components. After insulin addition, the mixture was homogenized using a pestle for 100 strokes to ensure uniform distribution of formulation, and the granules were dried using fluidized bed dryer at 25 degrees Celsius for 30 minutes. The dry granules were passed through a no. 16 sieve and stored at 4 degrees Celsius until further use.

Part B Components

| Components | weight |
|---|---|
| Labrasol ® | 600 mg |
| Glycerol | 100 mg |
| Water | 9000 mg |

Part B was prepared by, accurately weighing Labrasol® and glycerol and then suspend these components in water to form a dispersion.

Formulation 9 was prepared by combining part A and B shortly prior to oral administration (e.g., within 2 hours prior to oral administration).

Example 2

Droplet Size

An advantage of the formulations described herein is that insulin is contained within the aqueous core of droplets (which may include micelles and/or liposomes) which are spontaneously formed (optionally upon mild agitation) upon contact of the formulation with water or an aqueous solution. Because the size of such droplets influences their ability to traverse gastrointestinal surfaces (and thus affects the rate and extent of bioavailability of a drug contained within the liposomes), the size of droplets formed upon auto-emulsification of formulations described herein was analyzed.

In separate samples, one part of each of Formulations 1, 2, 3, and 4 was combined 500 parts of distilled water with gentle stirring and permitted to form a dispersion or an emulsion. The size of droplets thus formed was measured using a Zetasizer Nano ZS zeta potential analyzer (Malvern Instruments, Ltd.). The same instrument was used to measure the polydispersity index (PDI) for these emulsions. The calculations for the PDI parameter are defined in the ISO standard document 13321:1996 E and ISO 22412:2008. One part of Formulation 1 was combined 500 parts of 0.1 N HCl or phosphate-buffered saline (PBS) indicated that droplet sizes that are generally not larger than about 2000 nanometers, and other formulations described herein have droplet sizes that are generally not larger than about 800 nanometers.

Results of these experiments were as follows.

| Formulation | Average droplet size (nm) |
|---|---|
| Formulation 1 | 126 |
| Formulation 2 | 238 |
| Formulation 3 | 36 |
| Formulation 4 | 115 |

The average droplet size of Formulation 1 in 0.1 N HCl was 1822 nanometers. The average droplet size of Formulation 1 in standard phosphate-buffered saline was 873 nanometers.

Example 3

Acid Neutralization Studies

Formulation 1 was diluted ten-fold with a 4.2% (w/w) solution of sodium bicarbonate (i.e., one part Formulation 1 combined with nine parts of bicarbonate solution; final concentration 3.78%). The pH of this diluted composition was 8.2. The pH of 0.1N HCl is 1.2.

4.0 Milliliters of 0.1N HCl was combined with selected amounts of the diluted composition, and the pH of the resulting combined solution was measured. When HCl was combined with 1.0 milliliter of the diluted composition, the resulting pH was 5.64. When HCl was combined with 1.5 milliliter of the diluted composition, the resulting pH was 6.27. When HCl was combined with 2.0 milliliters of the diluted composition, the resulting pH was 6.48. These results demonstrate the acid-neutralizing effect of the Formulation/antacid combinations described herein. A skilled artisan can select an appropriate amount of antacid to neutralize anticipated amounts of stomach acid in humans and other subject (e.g., to raise the gastric pH to at least 3.0, to at least 3.4, or to any other desired value).

Example 4

Proteolytic Studies

Pepsin is a digestive protease in the stomach that exhibits significant proteolytic activity (including insulin-inactivating activity) between pH 1 and pH 3. The following experiments were performed to investigate the effect of pH on the pepsin-mediated inactivation of insulin contained within insulin-loaded formulations described herein.

Separately, 1 milliliter of Formulation 1 was combined with 9 milliliters of standard phosphate buffered saline to form a dispersion or an emulsion (the precise nature of the composition was not considered critical, and it is referred to as an "emulsion" hereafter). The pH of this emulsion was 6.9. The emulsion was then combined with 0.5 milliliter of simulated gastric fluid (1 gram sodium chloride, 3.5 milliliters 37% HCl in 500 milliliters of water) that included 1650 units of pepsin at a pH of either 1.4 or 3.4 (pH adjustment was with 0.1N NaOH). The mixtures were then incubated at 37° C. After 5, 30, or 90 minutes, the incubation was terminated in aliquots of the mixtures by adding 0.1 N NaOH (to change pH to the range of about 6-6.5 and thus halt pepsin activity).

Pepsin-mediated cleavage of insulin was assessed in each of the aliquots using HPLC by detecting expected insulin cleavage products. No intact insulin was observed in aliquots incubated at pH 1.4 for 5, 30, or 90 minutes, suggesting that rapid proteolytic cleavage of insulin had occurred. Essentially all insulin remained intact in aliquots which had been incubated for 30 and 90 minutes incubation at pH 3.4

(insulin was not assessed in an aliquot incubated for only 5 minutes at pH 3.4), suggesting that a pH of 3.4 rendered pepsin sufficiently inactive to maintain insulin in an uncleaved form during these periods. These results also suggest that raising the gastric pH of a subject to pH 3.4 (or at least to 3.0) permits insulin to remain intact in the gastric space when orally administered in formulations described herein.

Example 5

In Vitro Intestinal Permeability Studies

Experiments described in this example demonstrated that insulin can be transported across Caco-2 cell monolayers, which are known to resemble enterocyte cell layers which line the small intestine. These experiments were therefore considered indicative of ability of the formulations described herein to transport hydrophilic drugs such as insulin across the intestinal lining.

Caco-2 cells were cultured at 37±2 degrees Celsius in minimum essential medium (MEM) with Eagles salt and 1-glutamine supplemented with 15% fetal bovine serum, with 1% of non-essential amino acid, and with 1% of antibiotic-antimycotic in a incubator under a 5% carbon dioxide atmosphere to simulate intestinal lining cells. Cell monolayers which exhibited transepithelial electrical resistance values greater than 300 Ohms per square centimeter 21-28 days after seeding were used for this study.

At time zero, medium on one face of the cell monolayer was replaced by 0.5 milliliter of a solution that included one of Formulation 1, 2, or 3 or of insulin not incorporated into a SMEDDS-containing formulation. The solution was diluted ten-fold with medium (i.e., one part insulin-containing solution and nine parts buffer) prior to application to the monolayer. Thirty minutes following this replacement, insulin content at the basolateral face of the monolayer was analyzed by HPLC. The permeability coefficient (Papp) was calculated from the following equation: Papp=(dQ/dt)/($C_0$× area), where dQ/dt is the linear appearance rate obtained from the profile of the transported amount of the substrate against the time (measured in micrograms per second); $C_0$ is a measured initial concentration in the donor compartment (measured in micrograms per milliliter), and "area" is the membrane surface area of the cell monolayer.

No trans-monolayer transport of free insulin (i.e., insulin not combined with a SMEDDS-containing composition) could be detected after 30 minutes incubation. Values of Papp were determined to be: for monolayers to which diluted Formulation 1 was applied, $12\times10^{-6}$ centimeters per second; for monolayers to which diluted Formulation 2 was applied, $16\times10^{-6}$ centimeters per second; and for monolayers to which diluted Formulation 3 was applied, $9\times10^{-6}$ centimeters per second.

These results demonstrated that administration of insulin to cultured Caco-2 cell monolayers in diluted SMEDDS formulations described herein significantly enhanced transport of insulin across the monolayer. Because Caco-2 cell monolayers form tight junctions and are believed to be an appropriate model of enterocyte cell layers which line the small intestine, the results of these experiments are indicative of ability of the formulations described herein to transport hydrophilic drugs such as insulin across the intestinal lining.

Example 6

In Vivo Hypoglycemic Study with SMEDDS Containing Insulin Combined with Antacids after Oral Administration in Diabetic Mice, Normal Rats, and Healthy Beagle Dogs Diabetes was induced in male C57BL/6JNarl mice (8 weeks age, around 20 grams body weight) by two tail vein injections of streptozotocin (STZ) (first: 75 mg/kg, second: 150 mg/kg). Induction of diabetes in mice was verified by measuring glucose concentration in a blood sample that was obtained from the tail vein. Blood glucose levels of mice greater than 300 mg/dL were considered confirmation of induction of diabetes and mice exhibiting such levels ("STZ-induced diabetic mice") were used in the experiments described in this Example.

An composition containing 200 IU/kg of insulin was administered by oral gavage to each of eight STZ-induced diabetic mice in three groups (i.e., 24 mice total). A first group each received free non-modified insulin suspended in about 160-230 microliters (depending on animal weight) of a 3.78% (w/w) $NaHCO_3$ antacid solution. A second group each received insulin in the form of Formulation 1 suspended in about 160-230 microliters of phosphate-buffered saline (PBS). A third group received Formulation 1 insulin in the form of Formulation 1 suspended in about 160-230 microliters of a 3.78% (w/w) $NaHCO_3$ antacid solution (i.e., a ten-fold dilution of Formulation 1). Gastric pH was expected to increase above 3.4 shortly (i.e., within 0-3 minutes) following gavage for the first and third groups, and no substantial change in gastric pH was expected following gavage in the second group.

Blood samples were drawn from each mouse following gavage, and blood glucose levels in those samples were determined. The results of these blood glucose determinations are shown in FIG. 1.

STZ-induced diabetic mice in the third group (to which insulin in Formulation 1 together with antacid were administered) exhibited a substantial drop in blood glucose level, beginning as soon as 15 minutes following oral gavage and enduring for not more than about 4 hours. During the first 15 minutes following administration, the blood glucose level was decreased about 10% compared with that at time zero. Blood glucose levels of STZ-induced diabetic mice in the first (free insulin+antacid) and second (insulin in Formulation 1 without antacid) did not vary significantly over the remaining study period.

A roughly proportional dose-response was observed in groups of STZ-induced diabetic mice to which 50, 100, and 200 IU/kg of insulin was separately orally administered in Formulation 4 diluted with 3% $NaHCO_3$ as described herein. Of these mice, those which received 50 IU/kg of insulin exhibited an approximately 11% maximum reduction of blood glucose levels 30 minutes following administration, relative to initial levels; those which received 100 IU/kg of insulin exhibited an approximately 25% maximum reduction of blood glucose levels following administration; those which received 200 IU/kg of insulin exhibited an approximately 45% maximum reduction of blood glucose levels following administration.

Figure 4:
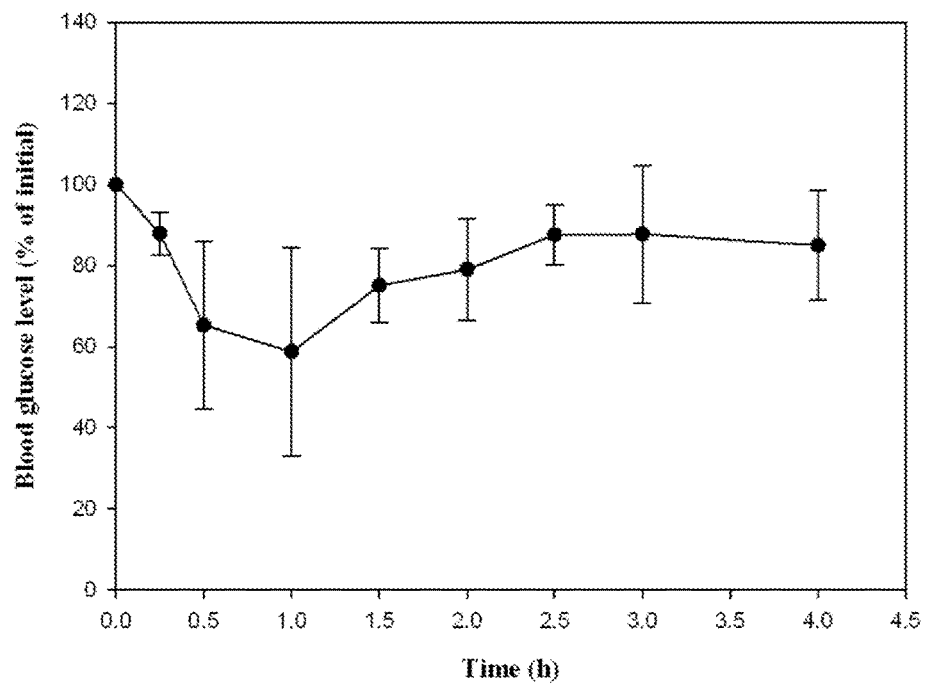
FIG. 4 is a graph of blood glucose levels over time, calculated as a percent of initial blood glucose values, for STZ-induced diabetic mice to which were orally administered 200 IU/kg of insulin in Formulation 2 suspended in a $NaHCO_3$ solution (final concentration 3.78%). Data shown are averages and standard deviations for groups of 8 mice each.
Figure 5:
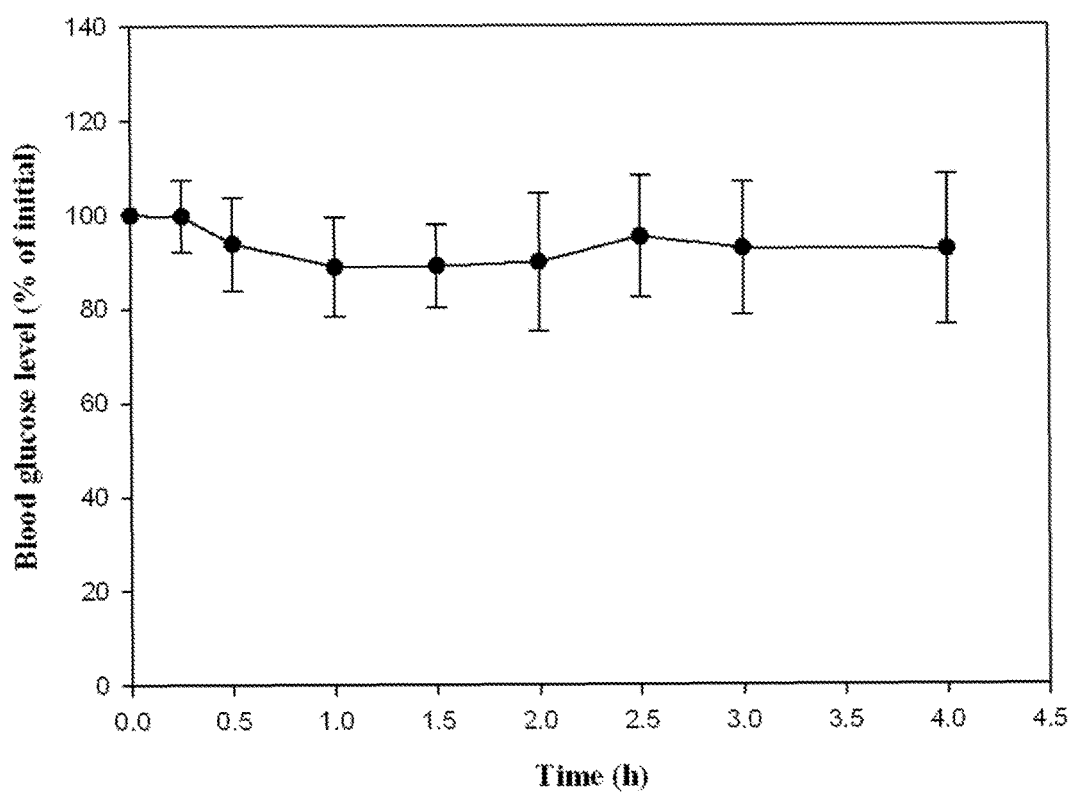
FIG. 5 is a graph of blood glucose levels over time, calculated as a percent of initial blood glucose values, for STZ-induced diabetic mice to which were orally administered 200 IU/kg of insulin in Formulation 3 suspended in a $NaHCO_3$ solution (final concentration 3.78%). Data shown are averages and standard deviations for groups of 8 mice each.
Figure 7:
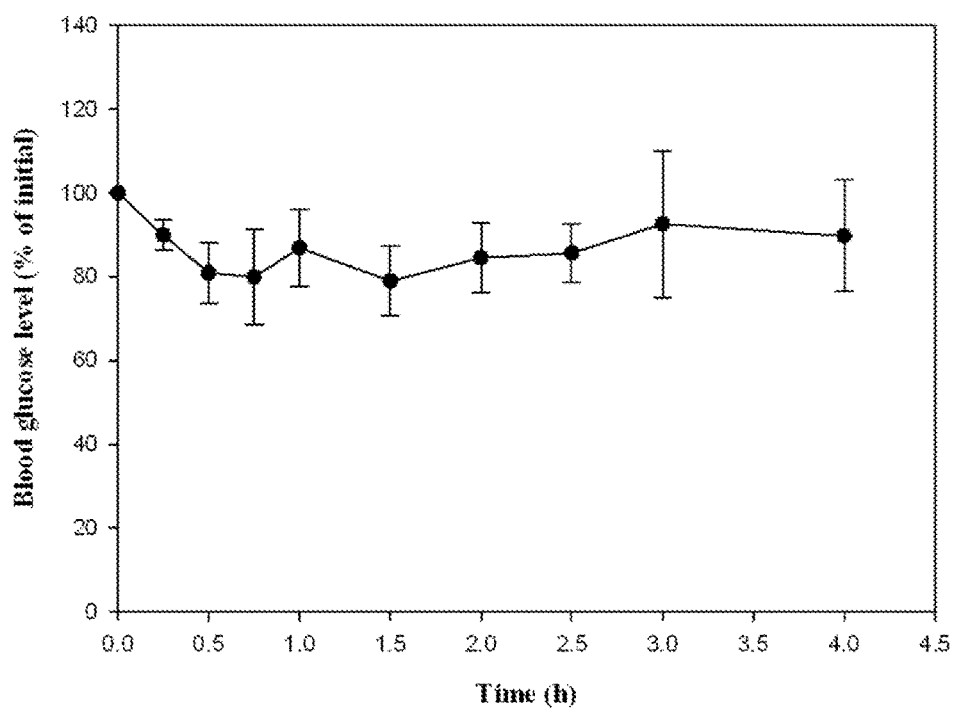
FIGS. 7 and 8 are graphs of blood glucose levels over time, calculated as a percent of initial blood glucose values, for STZ-induced diabetic mice to which were orally administered 50 IU/kg of insulin in Formulation 5, which included 8% $NaHCO_3$ (FIG. 7) or 50 IU/kg of insulin in Formulation 6, which included 2.1% $NaHCO_3$ and 0.9% $MgOH_2$ (FIG. 8).
Figure 8:
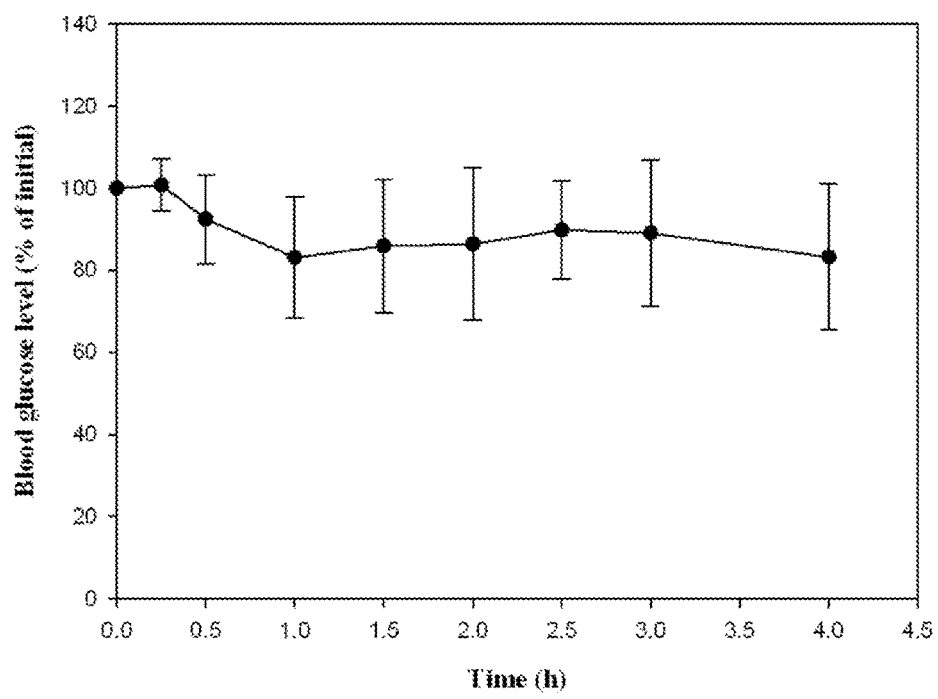
Figure 9A:
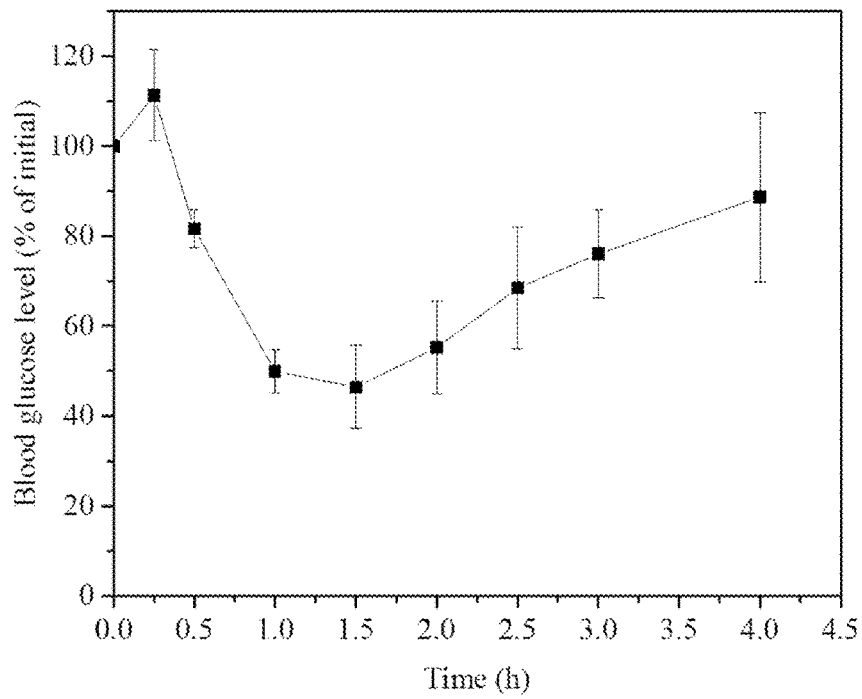
FIG. 9, consisting of FIGS. 9A and 9B, is a pair of graphs of blood glucose levels over time, calculated as a percent of initial blood glucose values, (FIG. 9A) and plasma insulin concentration over time (FIG. 9B) for STZ-induced diabetic Wistar rats to which were orally administered 200 IU/kg of insulin in Formulation 4. Data shown are averages and standard deviations for groups of 3 rats each.
Figure 9B:
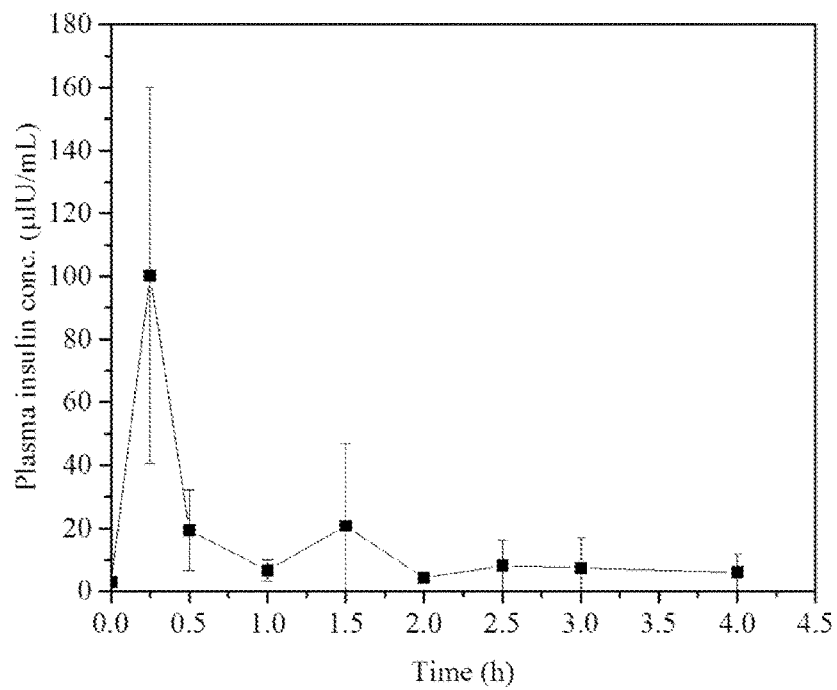

Similar results were observed in STZ-induced diabetic mice to which a ten-fold dilution of Formulation 2 in 3.78% $NaHCO_3$ was administered by oral gavage, as shown in FIG. 4 (200 IU/kg of insulin). Similar results were also observed when 50 IU/kg of insulin was administered by oral gavage to STZ-induced diabetic mice in the form of Formulation 5 together with 8% $NaHCO_3$ (see FIG. 7) or Formulation 6, which included 2.1% $NaHCO_3$ and 0.9% $Mg(OH)_2$ (see FIG. 8). For STZ-induced diabetic mice to which 200 IU/kg of insulin in Formulation 3 (a ten-fold dilution in 3.78% $NaHCO_3$) was orally administered, a decrease in blood glucose level was also observed, although the decrease was relatively slight (see FIG. 5). On the other hand, for STZ-induced diabetic Wistar rats to which was orally administered 200 IU/kg of insulin in Formulation 4, a similar profile of decreased blood glucose level was observed (see FIG. 9A) as were elevated blood insulin levels (see FIG. 9B).

Figure 10:
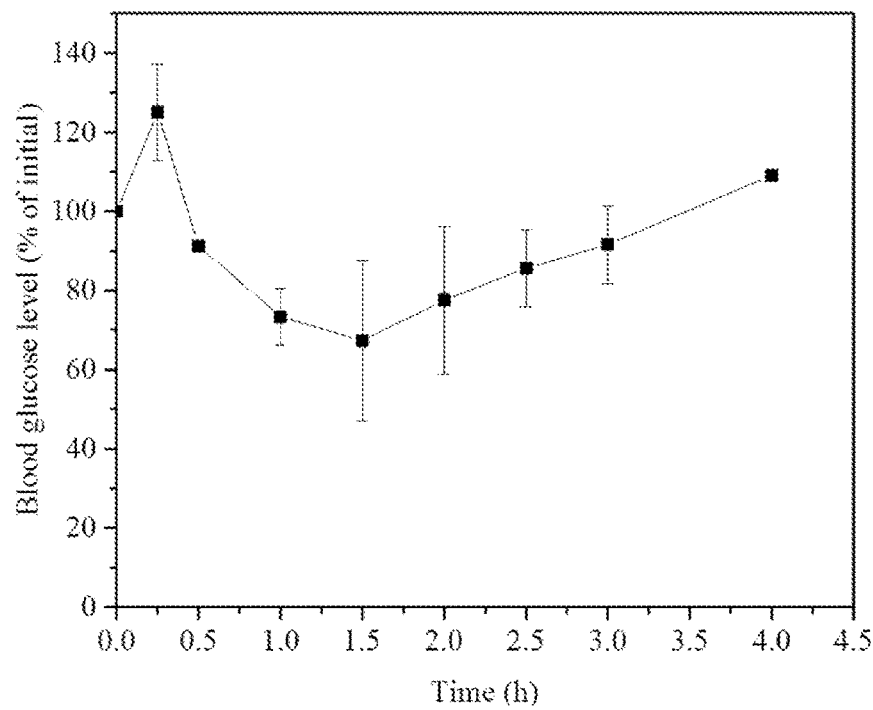
FIG. 10 is a graph of blood glucose levels over time, calculated as a percent of initial blood glucose values, for STZ-induced diabetic Wistar rats to which were orally administered 200 IU/kg of insulin in suspension after dispersion of Formulation 7 in water.
Figure 11:
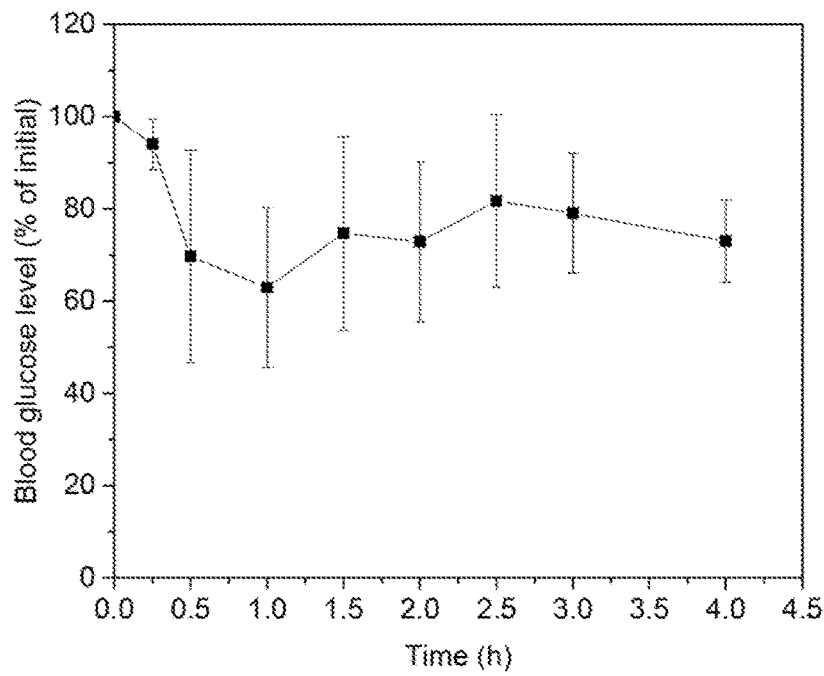
FIG. 11 is a graph of blood glucose levels over time, calculated as a percent of initial blood glucose values, for STZ-induced diabetic mice to which were orally administered 200 IU/kg of insulin in suspension after dispersion of Formulation 8 in water.
Figure 12:
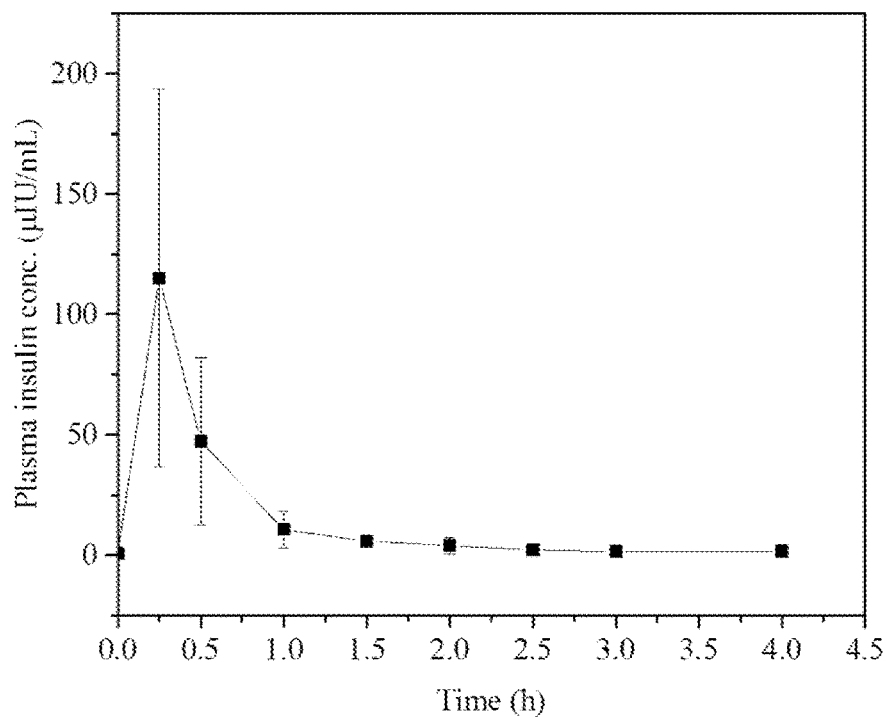
FIG. 12 is a graph of plasma insulin concentration over time for STZ-induced diabetic Wistar rats to which were orally administered 116 IU/kg of insulin in Formulation 9. Data shown are averages and standard deviations for groups of 5 rats each.

Formulations 7 and 8 were also effective for rapidly decreasing blood glucose level in STZ-induced diabetic Wistar rats or STZ-induced diabetic mice after administration, as shown in FIGS. 10 and 11. In addition, insulin (116 IU/kg) in Formulation 9 administered to STZ-induced diabetic Wistar rats, induced an increase of blood insulin concentration (see FIG. 12), indicating effective absorption of insulin from this formulation.

Figure 2:
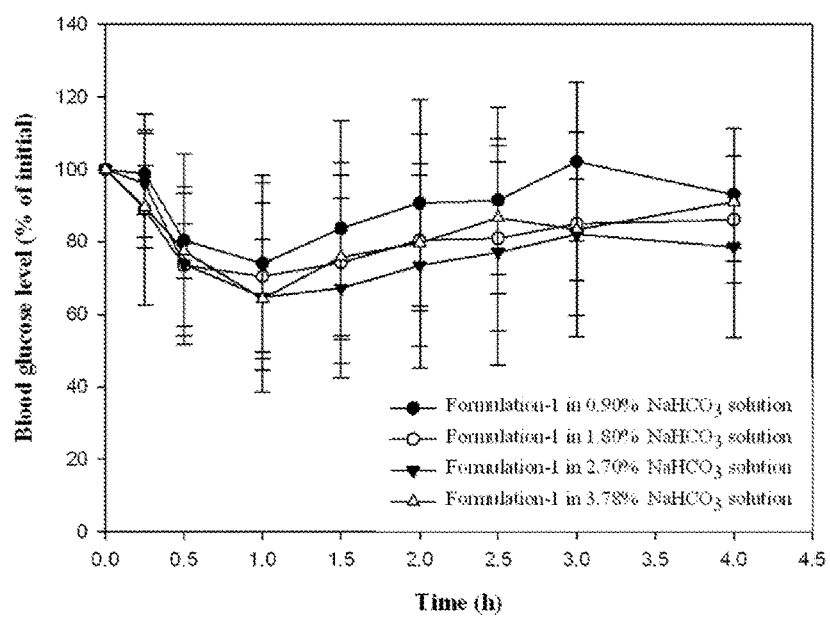
FIG. 2 is a graph of blood glucose levels over time, calculated as a percent of initial blood glucose values, for STZ-induced diabetic mice to which were orally administered 200 IU/kg of insulin in Formulation 1 suspended in $NaHCO_3$ solutions of varying final concentration. The final $NaHCO_3$ concentrations were: 0.90% (filled circles), 1.80% (open circles), 2.70% (filled triangles) and 3.78% (open triangles). Data shown are averages and standard deviations for groups of 8 mice each.

Results of experiments in which the $NaHCO_3$ content of the composition administered to STZ-induced diabetic mice by oral gavage was varied are shown in FIG. 2. Over the range of composition $NaHCO_3$ concentrations in the range 1.80-3.78% (w/w), there was little difference in blood glucose levels obtained, and some difference in blood glucose levels obtained when the $NaHCO_3$ concentration was reduced to 0.90% (w/w) was observable. These results suggest that an amount of antacid sufficient to depress gastric pH to 3.4 (or at least to about 3) shortly after oral administration is beneficial to insulin bioavailability via the oral route. Decreasing the bolus of antacid that is administered together with insulin can limit the overall bioavailability and shorten the duration of action of insulin. Therefore, the use of different amount antacid in the formulation can titrate (or adjust) the duration of action of insulin.

Figure 13:
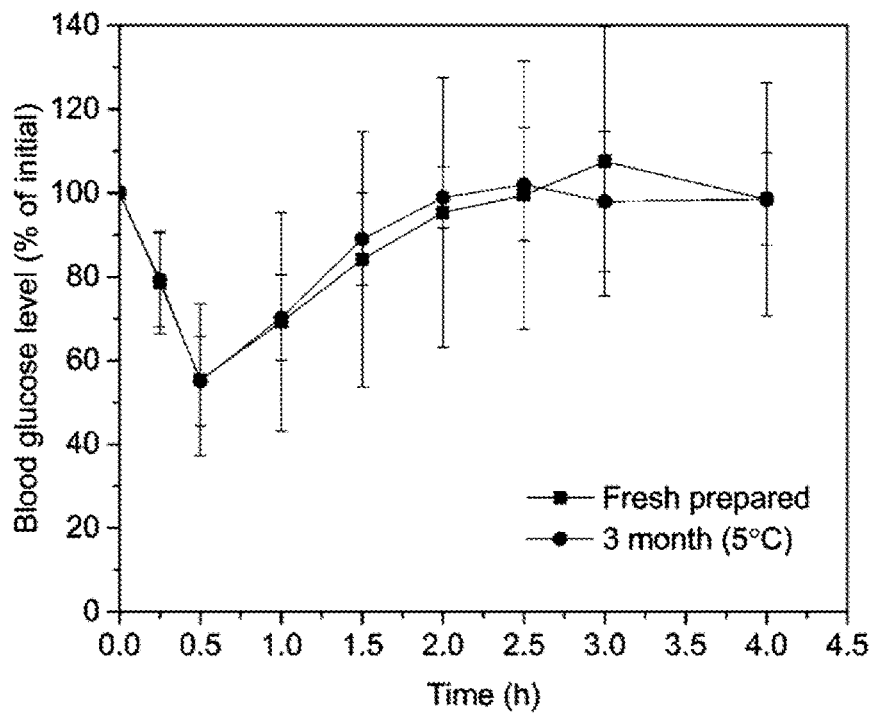
FIG. 13 is a graph of blood glucose levels over time, calculated as a percent of initial blood glucose values, for streptozotocin (STZ)-induced diabetic mice to which were orally administered 200 IU/kg of insulin in a 3.78% (w/v) aqueous solution of sodium bicarbonate ($NaHCO_3$) that was freshly prepared (filled squares) or that had been stored at 5 degrees Celsius for three months prior to administration (filled circles).

As illustrated in FIG. 13, the potency of orally administering Formulation 1 mixed with antacid to STZ-induced diabetic mice was unchanged if the composition was stored for three months at 5 degrees Celsius prior to administration (relative to freshly-prepared composition). These data illustrate that the compositions described herein are suitable for storage.

Figure 3:
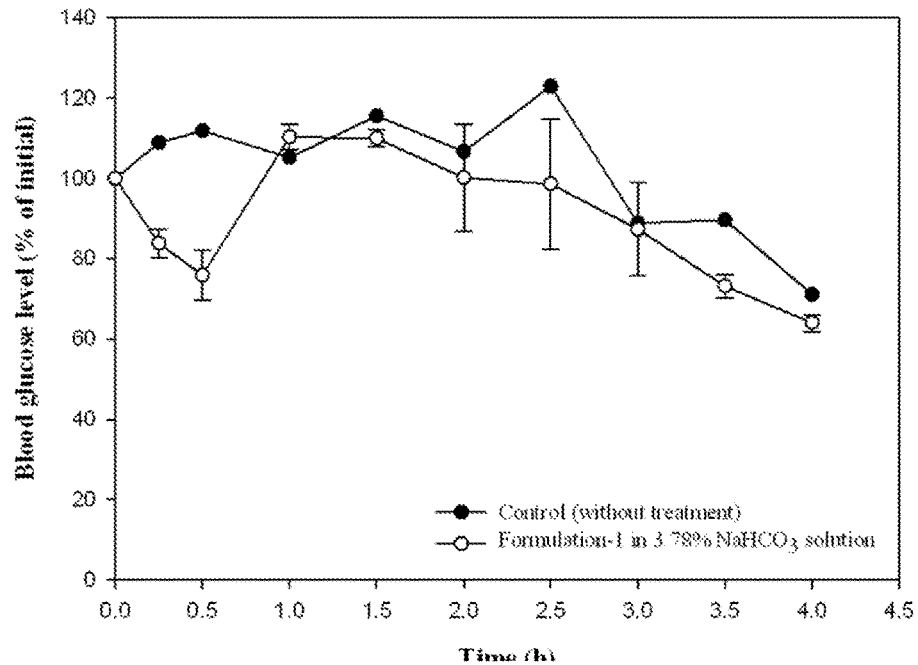
FIG. 3 is a graph of blood glucose levels over time, calculated as a percent of initial blood glucose values, for dogs to which were orally administered 150 IU/kg of insulin in Formulation 1 suspended in a $NaHCO_3$ solution (final concentration 3.78%; open circles) or for untreated control dogs (filled circles). Data shown are averages and standard deviations for groups of two beagle dogs each.

When non-modified insulin (150 IU/kg) was administered to healthy beagle dogs via oral gavage in a ten fold dilution of Formulation 1 in 3.78% $NaHCO_3$ (total volume 50 milliliters), similar results were observed, as indicated in FIG. 3. In FIG. 3, a rapid onset of insulin action is illustrated by a drop in blood glucose levels in treated dogs (open circles) 15 minutes following administration, relative to non-treated dogs (filled circles). The duration of action in dogs (not more than about 1 hour) appears to have been shorter in dogs than in mice, potentially owing to greater gastric acid production in dogs, relative to mice.

Figure 6A:
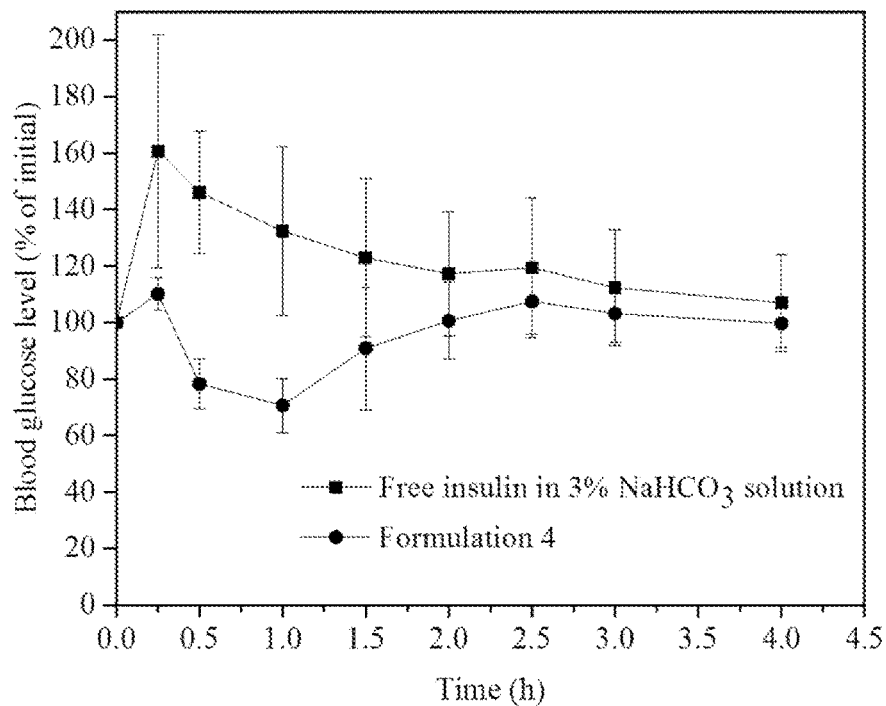
FIG. 6, consisting of FIGS. 6A and 6B, is a pair of graphs of blood glucose levels over time, calculated as a percent of initial blood glucose values, (FIG. 6A) and plasma insulin concentration over time (FIG. 6B) for normal Wistar rats to which were orally administered 200 IU/kg of insulin in Formulation 4 suspended in 3.00% $NaHCO_3$. Data shown are averages and standard deviations for groups of 3 rats each. Comparison data are also shown for rats to which free insulin suspended in a 3% $NaHCO_3$ solution was administered.
Figure 6B:
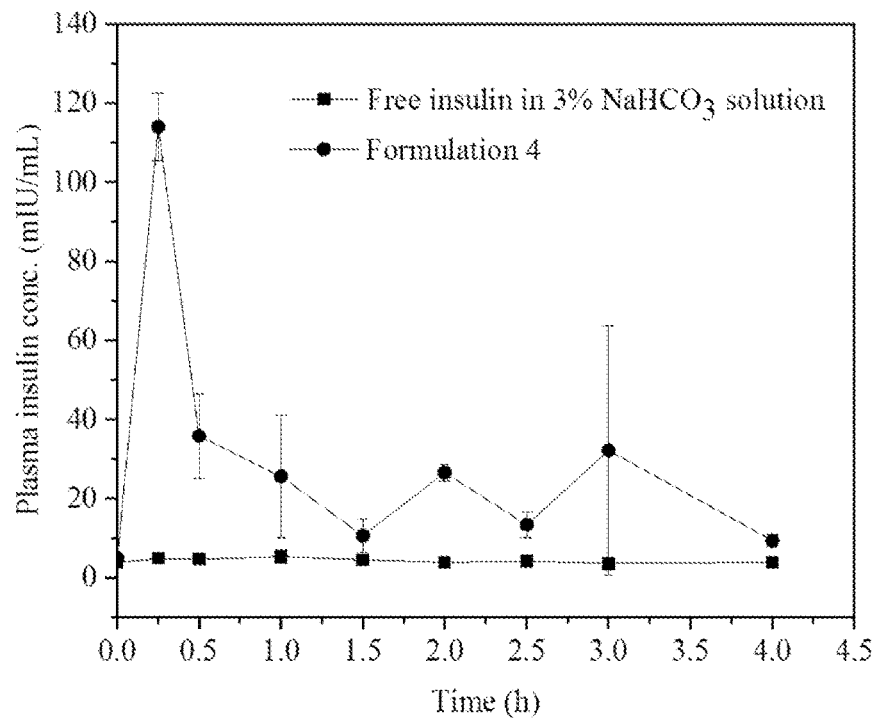

When non-modified insulin (200 IU/kg) was administered to normal Wistar rats via oral gavage in Formulation 4 in 3% $NaHCO_3$ (total volume 2.5-3.3 milliliters), results similar to those observed for mice and dogs are obtained, as illustrated in FIG. 6A. FIG. 6B shows insulin levels measured in these rats, confirming that the blood glucose-lowering effect is attributable to elevated blood insulin levels.

One of two insulin formulations were administered to beagle dogs to measure blood insulin concentration. The first formulation was Formulation 8, as described herein, and it was administered in the amount 25 IU per kilogram via the oral route after suspension in liquid. The second formulation was regular insulin, administered subcutaneously (SC) in aqueous suspension in the amount 0.5 IU per kilogram. Blood samples were obtained from dogs receiving the formulations at time 0 (i.e., immediately prior to administration) and at 15, 30, 60, 90, 120, 150, 180, and 240 minutes after administration. The results of these studies are shown in FIG. 15.

Taken together, the data shown in the Examples described herein demonstrate that formulation of insulin in a SMEDDS-containing composition and combination with an antacid bolus sufficient to raise gastric pH above about 3.0 renders insulin rapidly (i.e., within 15-30 minutes or less) available in mammalian subjects and can result in the insulin having a duration of action of about 2-4 hours. These data demonstrate that the formulations described herein can be effectively used to administer hydrophilic drugs which as sensitive to the acidic and/or proteolytic environment of the stomach, and that such formulations can be selected to yield rapid onset and limited duration of action of drugs so delivered.

Example 7

A rapid-acting oral insulin formulation was developed by using nanoemulsion solutions containing unmodified insulin (regular insulin). Rapid-acting insulin oral formulation begins to produce its physiological effects within 15 minutes of oral administration, and peak blood insulin levels occur at 30 minutes. Duration of activity was less than 3 hours. In addition, glucodynamic responses of oral insulin formulation were proportional to the dose administered. Stability studies showed that the potency and pharmacological action for this insulin formulation were stable after storage at 5 degrees Celsius for three months.

Insulin is usually administered via parenteral route because of proteolytic degradation and low permeability in the gastrointestinal tract. Injections are often painful, and can lead to low patient compliance. In contrast to inconvenience and discomfort of injected administration, the oral route of drugs is a comfortable and convenient route of administration. Many strategies such as liposomes, nanoparticles, microemulsion or enteric-coated capsule have been reported for improved oral delivery of insulin. At least some of these platforms provide effective absorption of insulin (Wong, 2010, J. Drug Target. 18(2):79-92; Arbit et al., 2009, J. Diabetes Sci. Technol. 3(3):562-567). However, none of those oral formulations were rapid-acting and short in duration.

Current experimental oral insulin formulations have a slow onset time (over 1.5 hours), and a long effective duration (over 5 hours). Rapid-action (onset within 15 minutes) and short duration (less than 5 hours) of orally-administered insulin, with effects analogous to insulin administered by IV injection, would provide a greater metabolic control (Mannucci et al., 2009, Diabetes Obes. Metab. 11(1):53-59). This is because appropriate timing of insulin administration results in a matching of postprandial carbohydrate absorption. Therefore, the purpose of the experiments described in this example was to develop rapid-acting short duration oral insulin formulation for oral administration, in order provide better metabolic control for patients with diabetes.

A rapid-acting oral formulation including regular (i.e., unmodified) insulin ("formulation insulin") was used in the studies described in this example. An in vivo hypoglycemia study was performed to investigate free insulin and formulation insulin via oral gavage in streptozotocin-induced diabetic mice (200 IU/kg) and healthy beagle dogs (150 IU/kg). Dose proportionality (doses of 50, 100, and 200 IU/kg) on the glucodynamic responses was also investigated in streptozotocin-induced diabetic mice.

The stability of rapid-acting oral insulin formulation was also investigated in this study. Insulin formulation samples were stored in closed glass screw-cap vials at 5 degrees Celsius for three months. Drug remaining in the formulation was analyzed, and in vivo potency was also assessed by administering insulin formulation into streptozotocin-induced diabetic mice and measuring blood glucose with a glucometer.

The results obtained in these studies are now described.

Blood glucose levels of streptozotocin-induced diabetic mice following oral administration with 200 IU/kg free insulin solution and rapid-acting oral formulation insulin is shown in FIG. 14. The maximum reduction (about 45%) of the initial blood glucose value was observed 0.5 hour after oral gavage of formulation insulin. Duration of activity was less than three hours. No significant differences in the blood glucose levels were found at any time point when free insulin solution was dosed by oral gavage.

Glucose reduction in the healthy beagle dogs after treatment with rapid-acting oral formulation insulin is shown in FIG. 3. The rapid-acting oral insulin formulation produced an average reduction in blood glucose level (about 25%) 0.5 hour post-dose, relative to the control. This finding was similar to the observations in hyperglycemic mice.

The following table shows the dose proportionality (doses of 50, 100, and 200 IU/kg) of rapid-acting oral formulation insulin on the glucodynamic responses. Average glucose reduction 0.5 hour post-dose showed a linear dose-response relationship.

| Dose (IU/kg) | Maximum reduction of blood glucose (% of initial) |
| --- | --- |
| 50 | 11 |
| 100 | 25 |
| 200 | 45 |

In-vitro potency of insulin formulations described herein after storage at 5 degrees Celsius for three months was assessed and indicated that 101.1±0.16% of insulin remained intact and available (data not shown). In vivo potency was assessed by administering formulation insulin to diabetic mice by oral gavage (results are shown in FIG. 13). There was no significant difference between the hypoglycemic profiles using freshly-prepared formulation insulin and formulation insulin stored for three months. These result confirmed the in vitro potency of formulation insulin after storage at 5 degrees Celsius for at least 3 months.

The information in this example indicates that the rapid-acting, short activity duration oral insulin formulation ("formulation insulin") described in this example exhibits dose proportionality, using doses of insulin 50, 100 and 200 III/kg. Both in vitro and in vivo studies showed no significant loss of potency and biological activity of insulin in formulation stored at 5 degrees Celsius for three months.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A dosage form for orally administering a gastrically impractical drug to the bloodstream of a mammal, the dosage form comprising an antacid sufficient to raise the gastric pH of the mammal to at least 3 upon ingestion of the dosage form; and a combination of a therapeutically effective amount of the drug and a surfactant system that includes a non-ionic surfactant, as a self-microemulsifying drug delivery system (SMEDDS), the identity and amount of the surfactant system being sufficient to induce spontaneous emulsification upon contact between the combination and an aqueous medium under conditions of mild mechanical agitation;

wherein the drug is an insulin peptide;

wherein the surfactant system includes

PEG-8 caprylic/capric glycerides, propylene glycol monolaurate and polyoxyethylene (20) sorbitan monooleate at ratios of: 40:3.3:1, and wherein the combination optionally further comprises a polyol solvent.

2. The dosage form of claim 1, wherein the antacid is selected from the group consisting of sodium bicarbonate, magnesium hydroxide, calcium carbonate, aluminum hydroxide, and combinations thereof.

3. The dosage form of claim 1, wherein the polyol solvent is selected from the group consisting of glycerol, propylene glycol, and polyethylene glycols.

4. The dosage form of claim 2, wherein the dosage form is a dosage form comprising an insulin peptide, PEG-8 caprylic/capric glycerides, propylene glycol, hydrochloride (HCl), propylene glycol monolaurate and polyoxyethylene (20) sorbitan monooleate, in combination with a sodium bicarbonate ($NaHCO_3$) solution, wherein the PEG-8 caprylic/capric glycerides, propylene glycol monolaurate and polyoxyethylene (20) sorbitan monooleate are at ratios of: 40:3.3:1.

5. A kit comprising the dosage form of claim 1 and an aliquot of the aqueous medium in an amount sufficient to dissolve or suspend the antacid and to emulsify the combination.

6. The dosage form of claim 1, wherein the dosage form is in a unitary dosage form or a multi-compartment dosage form.

7. The dosage form of claim 1, wherein the dosage form includes tablets, capsules, powder, granules, solution and/or suspension.

8. The dosage form of claim 1, wherein the dosage form is a homogenous composition.

9. A dosage form for orally administering an insulin peptide, comprising:

a therapeutically effective amount of the insulin peptide;

an antacid sufficient to raise the gastric pH of the mammal to at least 3 upon ingestion of the dosage form; and a surfactant system which comprises PEG-8 caprylic/capric glycerides, propylene glycol monolaurate and polyoxyethylene (20) sorbitan monooleates at ratios of: 40:3.3:1.

10. The dosage form of claim 9, wherein the dosage form is in a unitary dosage form or a multi-compartment dosage form.

11. The dosage form of claim 9, wherein the dosage form includes tablets, capsules, powder, granules, solution and/or suspension.

12. The dosage form of claim 9, wherein the dosage form is a homogenous composition.

* * * * *